United States Patent [19]

Vogt

[11] 4,337,255
[45] Jun. 29, 1982

[54] PYRAZOLO[1,5-C]QUINAZOLINE DERIVATIVES AND RELATED COMPOUNDS

[75] Inventor: B. Richard Vogt, Yardley, Pa.

[73] Assignee: E. R. Squibb & Sons, Inc., Princeton, N.J.

[21] Appl. No.: 925,740

[22] Filed: Jul. 19, 1978

Related U.S. Application Data

[62] Division of Ser. No. 820,289, Jul. 29, 1977, Pat. No. 4,128,644.

[51] Int. Cl.³ .................. A61K 31/505; C07D 487/04
[52] U.S. Cl. .................. 424/251; 424/248.5; 424/248.57; 544/115; 544/250; 548/373; 548/378; 548/483
[58] Field of Search .................. 544/250; 424/251

[56] References Cited

U.S. PATENT DOCUMENTS

| | | | |
|---|---|---|---|
| 3,895,027 | 7/1975 | Katner | 544/250 |
| 3,897,434 | 7/1975 | Katner | 544/250 |
| 3,903,106 | 9/1975 | Katner et al. | 544/250 |
| 4,083,980 | 4/1978 | Schromm et al. | 544/250 |

*Primary Examiner*—Glennon H. Hollrah
*Assistant Examiner*—James H. Turnipseed
*Attorney, Agent, or Firm*—Lawrence S. Levinson; Burton Rodney

[57] ABSTRACT

Compounds are provided having the structure

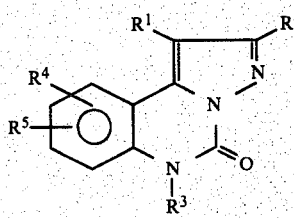

wherein R¹ is hydrogen, alkyl of 1-3 carbons, phenyl optionally substituted by R⁴; R² is cyano;

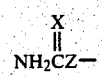

(wherein Z is a single bond or

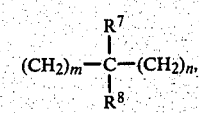

X is O or S);

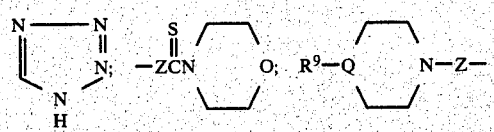

(wherein R⁹ is hydrogen or alkyl, Q is CH or N);

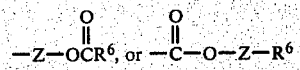

wherein R⁶ is amino, alkylamino, dialkylamino, haloalkyl or

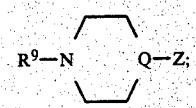

and R⁴ and R⁵ are the same or different and represent hydrogen, lower alkyl, lower alkoxy, alkanoyloxy, benzyloxy, substituted benzyloxy, hydroxy, halogen (Cl, Br and F), nitro and trifluoromethyl; and R⁷, R⁸, m and n are as defined hereinafter. The above compounds are useful as anti-allergy agents.

11 Claims, No Drawings

PYRAZOLO[1,5-c]QUINAZOLINE DERIVATIVES AND RELATED COMPOUNDS

This is a division of application Ser. No. 820,289, filed July 29, 1977, now U.S. Pat. No. 4,128,644.

The present invention relates to pyrazolo[1,5-c]quinazoline derivatives of the structure

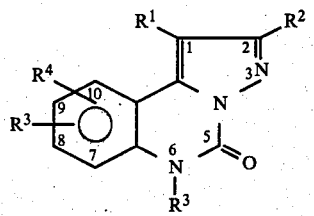

wherein $R^1$ represents hydrogen, lower alkyl (1–3 carbons), phenyl optionally substituted with $R^4$, $R^2$ is cyano;

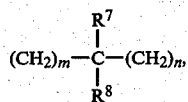

(wherein Z is a single bond or

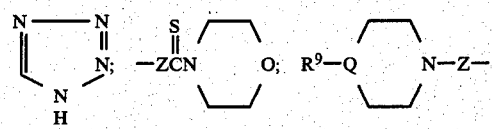

X is O or S);

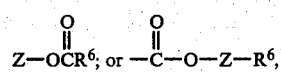

(wherein $R^9$ is hydrogen or alkyl, Q is CH or N);

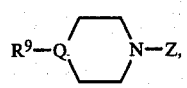

wherein $R^6$ is amino, alkylamino, dialkylamino, arylamino, or haloalkyl, or

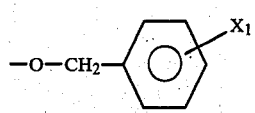

$R^3$ is hydrogen, lower alkyl, benzyl or phenyl optionally substituted by an $R^4$ radical as defined below;
$R^4$ and $R^5$ may be the same or different and are hydrogen, lower alkyl (1–4 carbons), lower alkoxy (1–4 carbons), hydroxy, alkanoyloxy (1–4 carbons),

($X_1$ is hydrogen, lower alkoxy (1–4 carbons), or $NO_2$);
$R^7$ and $R^8$ may be the same or different and represent hydrogen, lower alkyl containing 1–3 carbons, phenyl optionally substituted with $X_1$ or benzyl optionally substituted with $X_1$, $(CH_2)m$ and $(CH_2)n$ represent a single bond or stright or branched chain alkylene radicals; and m and n represent the number of carbons in the longest normal chain and may be the same or different and are 0 to 10, preferably 0 to 5, but m plus n is 10 or less, preferably 0 to 5.

Unless otherwise indicated the term "lower alkyl" or "alkyl" as employed herein includes both straight and branched chain radicals of up to eight carbon atoms, for instance, methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, and the like.

Unless otherwise indicated, the term "lower alkoxy" or "alkoxy" includes straight and branched chain radicals which correspond to the above lower alkyl groups attached to an oxygen atom.

Unless otherwise indicated, the term "lower alkanoyl" or "alkanoyl" as employed herein includes any of the above lower alkyl groups linked to a carbonyl group.

Unless otherwise indicated, the term "aryl" as employed herein contemplates monocyclic carbocyclic aryl radicals, for instance, phenyl and substituted phenyl radicals, such as lower alkyl phenyl (e.g., o-, m- or p-tolyl, ethylphenyl, butylphenyl, and the like), di(lower alkyl)phenyl (e.g., 2,4-dimethylphenyl, 3,5-diethylphenyl, and the like), halophenyl (e.g., chlorophenyl, bromophenyl, iodophenyl, fluorophenyl).

Unless otherwise indicated, the term "aroyl" includes any of the above aryl groups linked to a carbonyl group.

Thus, compounds encompassed by the structure of formula I include, but are not limited to, the following:

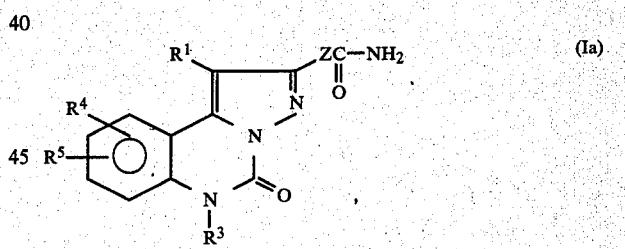
(Ia)

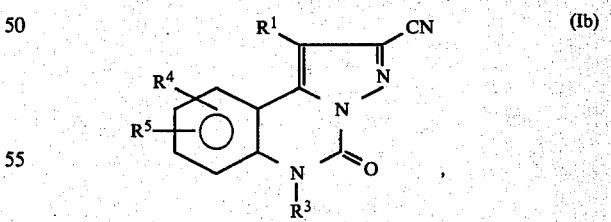
(Ib)

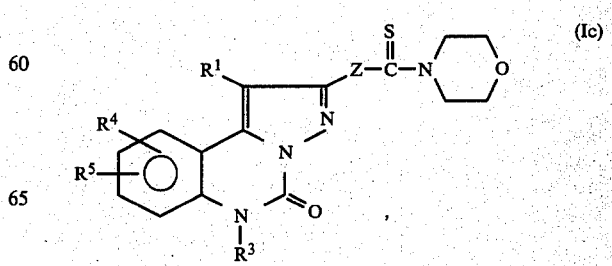
(Ic)

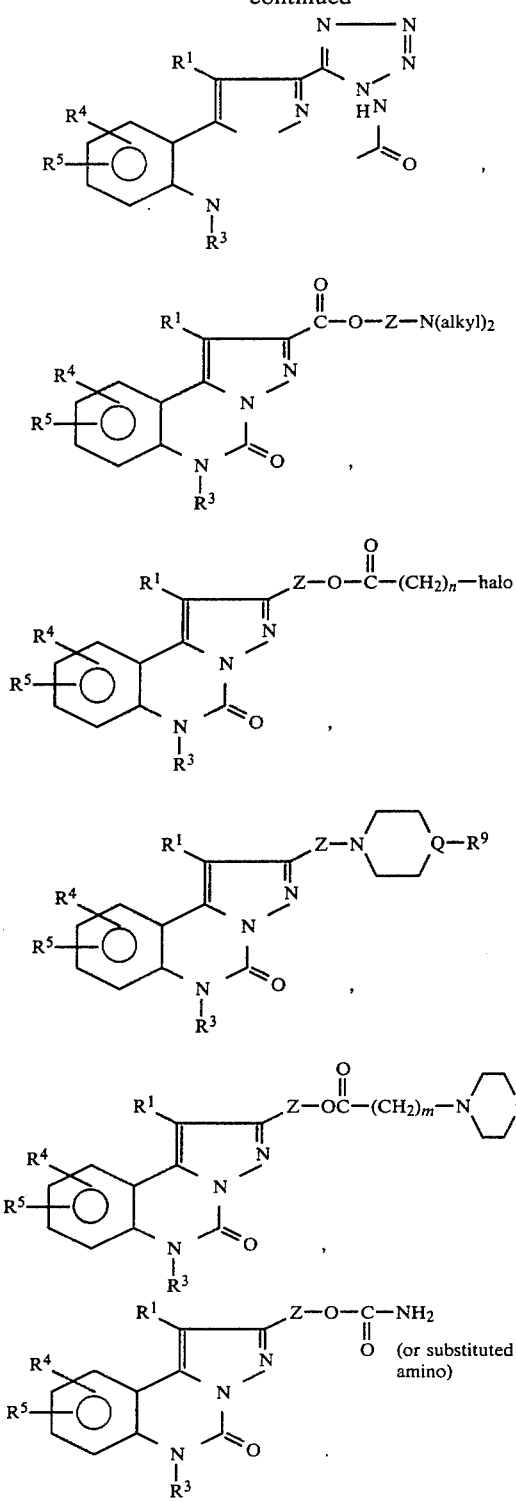

Preferred compounds of formulae Ia, Ib, Ic, Id, Ie, If and Ii are those wherein R⁴, R⁵ and R³ are hydrogen.

Preferred compounds of formulae Ig and Ih are those wherein Q is N, R⁹ is alkyl, and R³, R⁴ and R⁵ are hydrogen.

The compounds of Formula I of the invention may be prepared by several methods.

One such method involves the preparation of compounds of the structure

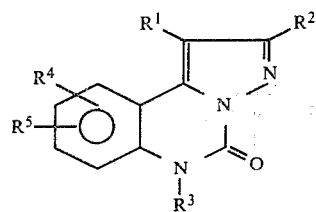

wherein $R^1$ to $R^5$ are as defined hereinbefore. This method (hereinafter called the "first method") involves reacting a substituted acetylene of formula III with a 3-diazoindol-2(3H)one of formula II in accordance with the following reaction scheme:

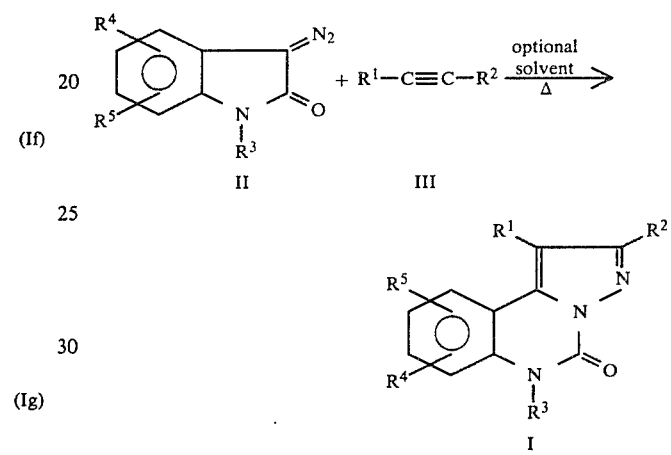

The reaction can be carried out in an excess of the acetylenic compound or in an optional solvent which is essentially inert to both of the reactants. Examples of suitable optional solvents include, among others, aliphatic hydrocarbons, such as pentane, hexane, octane, and the like; aromatic hydrocarbons, such as benzene, toluene, the xylenes, and the like; halogenated hydrocarbons, such as methylene chloride, chloroform, carbon tetrachloride, ethylene dichloride, chlorobenzene, bromobenzene, and the like; ethers, such as diethyl ether, diisopropyl ether, methyl butyl ether, tetrahydrofuran, 1,4-dioxane and the like; aliphatic esters, such as methyl acetate, ethyl acetate, butyl acetate, and the like; and miscellaneous solvents, such as N,N-dimethylacetamide, dimethyl sulfoxide, and the like. The aromatic hydrocarbons, such as benzene and toluene and the chlorinated hydrocarbons, such as methylene chloride are preferred. The amount of solvent employed is not critical, but should be sufficient to permit adequate agitation. Typically, the weight-to-volume ratio of reactants to solvent is at least about 1:2 and preferably at least about 1:3, although larger volumes of solvent can be employed if desired. The molar ratio of substituted acetylene to 3-diazoindol-2(3H)-one can vary from about 1:1 to about 100:1. Preferably, the molar ratio will be in the range of from about 1:1 to about 40:1. Reaction time, while to some extent temperature-dependent, can vary from about 15 minutes to about 48 hours. Preferably, the reaction time will be in the range of from about 15 minutes to about 30 hours. The reaction is normally carried out at an elevated temperature, i.e., from about 40° C. to about 150° C., conveniently at the reflux temperature of the solvent, if used, or below about 150° C.

A reaction temperature of from about 70° C. to about 120° C. is preferred. Isolation of the compounds of formula I is accomplished by standard procedures. With the preferred optional solvents, the pyrazolo[1,5-c]quinazolin-5(6H)-one is relatively insoluble at ambient temperature or lower, and isolation of the reaction product is accomplished by cooling the reaction mixture and removing the precipitate.

In the absence of solvent, the remaining excess substituted acetylene can be optionally removed by distillation in vacuo; the product is isolated by triturating the distillation residue with a preferred solvent followed by filtration of the precipitated product. If desired, the pyrazolo[1,5-c]quinazolin-5(6H)-one can be recrystallized from additional reaction solvent.

Another synthesis of compounds of formula I starts with the preparation of compounds of formula V wherein $R_1^1$ is

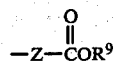

($R^9$ is H, lower alkyl, phenyl or benzyl),

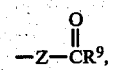

H, alkyl (1-2 carbons), and $R_1^2$ is ZOH (wherein $R^2$ in formula I is to be

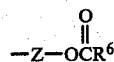

where $R^6$ is haloalkyl) or

(where $R^2$ in formula I is to be

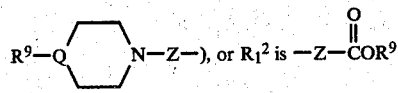

(wherein $R^2$ in formula I is to be

or $R_1^2$ is

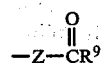

(wherein $R^2$ in formula I is to be

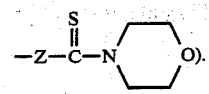

Compounds of formula V are prepared by reacting a substituted acetylene (IV) with a 3-diazoindol-2(3H)-one (II) (in a fashion similar to that of the first method) in accordance with the following reaction scheme:

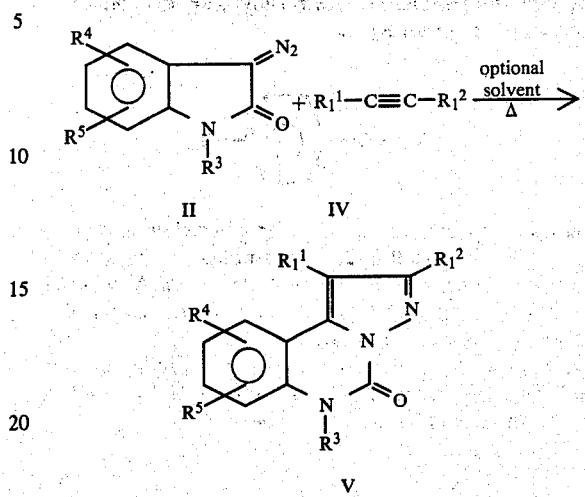

wherein $R_1^1$ and $R_1^2$ are as defined above. In the examples where Z is a single bond, the reaction is preferably carried out in a solvent and the mole ratio of substituted acetylene to 3-diazoindol-2(3H)-one is preferably in the range of 1:1 to about 3:1.

Thus, compounds of formula Ic may be prepared by reacting a compound of the structure

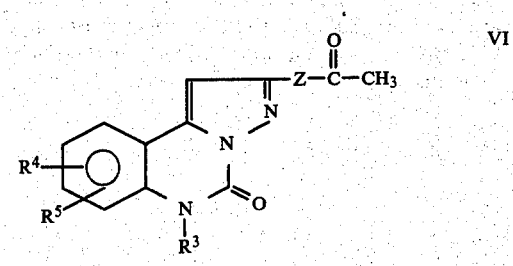

with sulfur and morpholine at a temperature ranging from about 40° to about 220° C. for from 0.5 hour to 48 hours.

Compounds of formula Id may be prepared by reacting a carbonitrile compound of formula Ib with an alkali metal azide in the presence of ammonia or ammonium salt in an aprotic solvent, such as dimethyl formamide, at temperatures ranging from about 60° to about 180° C. for periods ranging from about 0.5 hour to about 48 hours.

Compounds of formula Ie may be prepared by reaction of compounds of formula V wherein $R_1^2$ is

(prepared from the corresponding carboxylic acid, for example, by reaction with a basic sodium salt and oxalylchloride) with an amino alcohol in the presence of a basic solvent such as pyridine.

Compounds of formula If are prepared from the corresponding alcohol derivative of formula V wherein $R_1^2$ is $(CH_2)_m$—OH (prepared by reduction of the corresponding ester or by the second method using the appropriately substituted acetylene) by reacting the alcohol derivative with a haloalkanoic acid (Hal—$(CH_2)_m$—COOH).

Compounds of the formula Ig are prepared by reacting the corresponding phenylsulfonate derivative of formula V wherein $R_1^2$ is

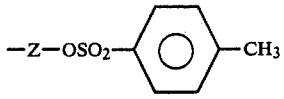

with the appropriately substituted piperidine or piperazine. The phenylsulfonyloxy compound is prepared by reacting the appropriate alcohol of formula V wherein $R_1^2$ is —Z—OH with tosyl chloride in the presence of a basic solvent such as pyridine.

Compounds of the formula Ih are prepared from corresponding compounds of formula If by reacting same with a compound of the structure

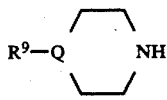

VII in the presence of an inert solvent such as 1,2-dimethoxyethane under $N_2$.

Compounds of the structure of formula Ii are prepared from compounds of formula V wherein $R_1^2$ is —Z—OH by reacting same with an alkali metal cyanate and trifluoroacetic acid in the presence of a hydrocarbon solvent such as benzene. Compounds of formula Ii wherein $R_1^2$ is

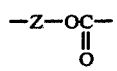

(substituted amino), such as

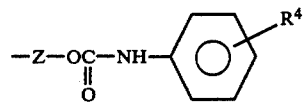

are prepared from compounds of formula V wherein $R_1^2$ is —Z—OH by reacting same with the appropriately substituted phenyl isocyanate in the presence of a basic solvent such as pyridine.

The substituted acetylenes employed in the above-described processes in general are commercially available or readily prepared by well-known procedures. For example, substituted acetylenes of the structure

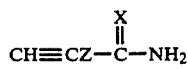

VIII may be prepared by reacting the acetylene

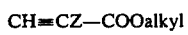    IX with liquid ammonia for 10 to 20 hours.

Cyanoacetylene of the structure

is prepared by reaction of propiolamide

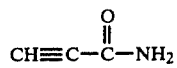    XI with phosphorus pentoxide at temperatures up to 200° C.

The 3-diazoindol-2(3H)-ones employed in the above-described processes in general are prepared from the corresponding isatin compound. The preparation of isatin compounds is well known in the art. The required N-substituted isatin is obtained by either of two routes, depending upon whether the N-substituent is (1) alkyl or aralkyl, or (2) aryl. When the desired isatin nitrogen substituent is alkyl or aralkyl, the isatin compound is prepared by N-alkylation of the parent compound with an alkyl or aralkyl halide in the presence of a strong base such as, for example, sodium hydride. However, when an aryl substituent on the isatin nitrogen is desired, a different procedure must be employed. In that case, the desired N-aryl isatin is prepared directly by cyclization with oxalyl chloride of an appropriately-substituted diarylamine.

Once the desired isatin has been obtained, the corresponding 3-diazoindol-2(3H)-one is prepared in accordance with known procedures. See, for example, J. M. Michowski, *Tetrahedron Letters*, 1773 (1967) and M. P. Cava, et al., *J. Am. Chem. Soc.*, 80, 2257 (1958). The appropriate isatin compound is treated with p-toluenesulfonylhydrazine. The resulting hydrazone then is treated with a base such as aqueous sodium hydroxide or aluminum oxide to give the desired 3-diazoindol-2(3H)-one.

The compounds of formula V wherein

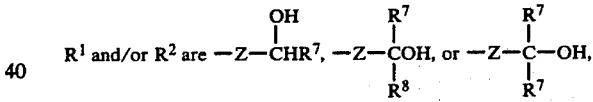

(wherein $R^4$ and $R^5$ are other than hydroxy, alkanoyloxy, or halogen), are also prepared by reacting compounds of formula V wherein $R_1^1$ and/or $R_1^2$ are

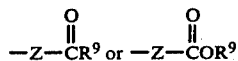

(wherein $R^9$ is other than hydrogen), with alkyl, phenylalkyl and phenyl Grignard reagents of the formula

    XII wherein $X_2$ is Cl or Br and $R^9 \neq H$, or with alkyl, phenylalkyl and phenyl lithium reagents of the formula

    XIII wherein $R^9 \neq H$.

Compounds of formula V wherein $R_1^1$ and/or $R_1^2$ are

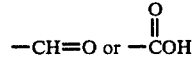

are prepared by selectively oxidizing compounds of formula V wherein $R_1^1$ and/or $R_1^2$ are methyl (or hydroxymethyl) with selective oxidizing agents such as chromyl chloride or chromic acid (or manganese dioxide), respectively, in essentially non-reactive solvents such as carbon disulfide or acetic acid-sulfuric acid mixtures, (or in chloroform) respectively.

Where the $R_1^1$ or $R_1^2$ groups represent

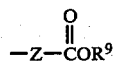

and

then the total number of carbons in the Z group will be 3 or less. Where $R_1^1$ or $R_1^2$ is

wherein $R^9$ is lower alkyl or

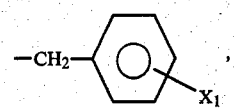

then the total number of carbon atoms in the

lower alkyl group or

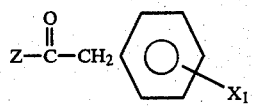

group will be 4 or less.

The reaction can be run in an inert aprotic organic solvent such as an ether like diethyl ether, tetrahydrofuran, or 1,2-dimethoxyethane at a temperature of $-70°$, or just above the freezing point of the reaction mixture, to 100° C. for 0.5 to 72 hours. The products are isolated by cooling, neutralization with mild acid, and extraction.

Compounds of formula V wherein $R_1^1$ and/or $R_1^2$ are

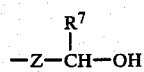

and where $R^4$ and/or $R^5 \neq$ alkanoyloxy are also prepared by several other methods. One general method involves selectively reducing (chemically or by catalytic means) the compounds of formula V wherein $R_1^1$ and/or $R_1^2$ are

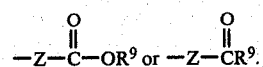

Exemplary of the chemical reduction processes is the reaction of a compound of formula V wherein $R_1^1$ and/or $R_1^2$ are

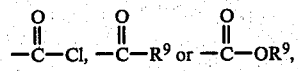

with metal hydrides, such as aluminum hydride; substituted metal hydrides, such as diisobutyl aluminum hydride; complex metal hydrides, such as magnesium aluminum hydride, sodium aluminum hydride, aluminum borohydride, calcium borohydride and the like, alkoxyaluminum hydrides, such as sodium di-(2-methoxyethoxy)aluminum hydride and the like; and of compounds of formula VI wherein $R_1^1$ and/or $R_1^2$ are any of the above other than -COOH, with complex metal hydrides, such as lithium borohydride or sodium dimethoxy borohydride; and wherein $R_1^1$ and $R_1^2$ are $$-\overset{O}{\underset{\|}{C}}-Cl \text{ or } -\overset{O}{\underset{\|}{C}}-R^9$$

with complex metal hydrides, such as potassium borohydride and sodium borohydride, and mixtures of the above with magnesium and aluminum chlorides and bromides.

The reaction can be run in inert non-hydroxylic organic solvents, such as ether (4-12 carbons), for example, diethyl ether, diisopropyl ether, diphenyl ether, tetrahydrofuran, dioxane, 1,2-dimethoxyethane and the like; saturated hydrocarbons (6-10 carbons), such as n-hexane, cyclohexane; aromatic hydrocarbons (6-10 carbons), such as benzene, toluene, xylene; halogenated hydrocarbons (1-4 carbons), such as methylene chloride, chloroform, dichloroethane, tetrachloroethane; or, where compatible with the less reactive reducing agents, such as sodium borohydride, in alkanols (1-6 carbons) such as methanol, isopropanol or, preferably, ethanol, at a temperature of 25° C. to reflux for 0.5 hour to 48 hours.

Other chemical reducing agents which can be used in the process of this invention include (wherein $R_1^1$ and/or $R_1^2$ are

aluminum and sodium alkoxides in the presence of the corresponding alcohol, e.g., aluminum isopropoxide in isopropanol; (wherein $R_1^1$ and/or $R_1^2$ are

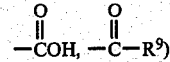

borane in inert non-hydroxylic solvents such as ethers like tetrahydrofuran; ethyl ether; (wherein $R_1^1$ and/or $R_1^2$ are

dialkylboranes such as di(1,2-dimethylpropyl)borane in inert non-hydroxylic solvents as above.

Compounds of formula V wherein $R_1^1$ and/or $R_1^2$ are $CH_2(CH_2)_nCH_2OH$ can also be prepared via a Willgerodt-Kindler reaction by reacting appropriate compounds of formula I, wherein $R^1$ and/or $R^2$ is

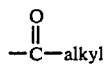

(wherein alkyl is of the formula $-(CH_2)_nCH_3$), with sulfur and ammonium hydroxide or sulfur with an amine, such as morpholine, or with ammonium polysulfide at from about 40° C. to about 220° C., preferably 80° C. to 180° C., for from 0.5 hour to about 48 hours, preferably 2 to 24 hours.

The product of formula V wherein $R_1^1$ and/or $R_1^2$ is the corresponding thioamide, e.g.,

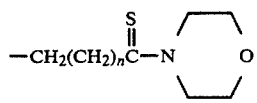

(from the reaction where $R_1^1$ and/or $R_1^2$ is

with sulfur and morpholine) is hydrolyzed in, for example, refluxing concentrated HCl to give the corresponding acid of formula I where $R^1$ and/or $R^2$ is $-CH_2(CH_2)_nCO_2H$.

Reduction of the above acid with a selective chemical reducing agent such as diborane in tetrahydrofuran gives the alcohol of formula V wherein $R_1^1$ and/or $R_1^2$ is $CH_2(CH_2)_{n+1}OH$.

Compounds of formula V wherein one of $R_1^1$ and $R_1^2$ is hydrogen; alkyl (1-3 carbons); phenyl; phenyl substituted with $X_1$ [that is alkyl (1 to 4 carbons), alkoxy (1 to 4 carbons)], benzyl; or benzyl substituted with $X_1$; and the other of $$R_1^1 \text{ and } R_1^2 \text{ is } Z-\overset{O}{\underset{\|}{C}}-OR^9 \text{ or } Z-\overset{O}{\underset{\|}{C}}R^9,$$

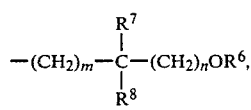

or where $R_1^1$ and $R_1^2$ are the same and are

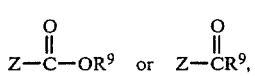

and where $R^6$ and $R^9 \neq H$, and where $R^4$ and $R^5 \neq OH$ are prepared by reacting compounds of the structure

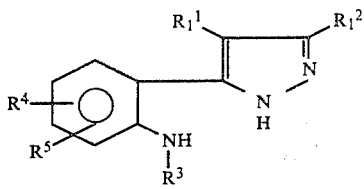

with phosgene in the presence of a base, such as alkali metal hydroxide, alkaline earth metal hydroxide or quaternary ammonium hydroxide or a heterocyclic amine, such as pyridine. The reaction is carried out in the presence of an inert organic solvent such as chlorinated hydrocarbons, for example methylene chloride or ethylene chloride, or aromatic hydrocarbons such as benzene, at temperatures ranging from about 0° C. to reflux for periods of 0.5 to 48 hours.

Other cyclizing agents which may be employed in carrying out the above reaction include: 1,1'-carbonyldiimidazole in a halogenated aromatic solvent, e.g., o-dichlorobenzene, at 50° to reflux temperature, for 1 to 48 hours (preferably 1 to 24 hours); sodium hydride and 1-ethoxycarbonylimidazole in an ether, e.g., tetrahydrofuran, refluxed for 3 hours; urea at 200°; ethyl carbamate and $ZnCl_2$ at 190° (for 4 hours); and KNCO in acetic acid at 60° (for 6 hours).

Compounds of formula VIII where $R^3=H$ can be prepared by several methods such as from the corresponding nitro substituted compound

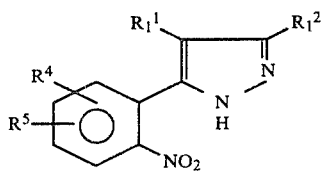

by employing conventional selective chemical reduction or catalytic hydrogenation techniques, such as sodium sulfite, tin and HCl, zinc and acetic acid or hydrogen and Raney nickel, respectively.

The esters of formula V wherein $R_1^1$ and/or $R_1^2$ are $Z-CO_2R^9$ ($R^9 \neq H$) may be prepared from the corresponding carboxylic acids of formula V wherein $R_1^1$ and/or $R_1^2$ are Z-COOH by known esterification procedures such as (1) alkylation of alkali metal or trialkylammonium salts of the above acid with alkyl or aralkyl halides, e.g., methyl iodide, benzyl chloride; (2) alkylation of the carboxylic acid with diazoalkanes and diazoaralkanes, e.g., diazomethane; (3) conversion of the carboxylic acid to the corresponding acid chloride or acid bromide (e.g., by reaction of the above carboxylic acid salts with a slight excess of, for example, oxalyl chloride or thionyl chloride) and subsequent reaction with the appropriate alcohol, in the optional presence of a catalyst such as pyridine in e.g., methylene chloride.

Compounds of formula V wherein $R_1^1$ and/or $R_1^2$ are —COOH, and/or $R^3$ and/or $R^4$ and/or $R^5$ are OH are prepared by reacting compounds of formula V, wherein $R_1^1$ and/or $R_1^2$ are and/or $R^4$ and/or $R^5$ are

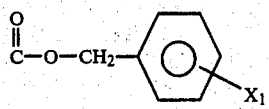

and/or $R^4$ and/or $R^5$ are

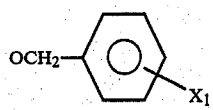

and $R^3$ is

with an appropriate reducing agent under selective conditions in an inert organic solvent.

Typical reducing agents include a metal catalyst, preferably Raney nickel, and hydrogen in the optional presence of a hydrogen halide in an inert organic solvent. Typical solvents include alkanols of 1–6 carbons such as methanol, ethanol and the like. The preferred optional hydrogen halides are hydrogen chloride and hydrogen bromide. The reactions are carried out for from about 1/6 hour to about 92 hours, preferably for from about ½ to about 24 hours at from about −20° to about 100° C.

The last-mentioned compounds of formula V can also be prepared by reacting the last-mentioned starting materials of formula V with at least about 0.5, preferably at least about 0.8, molar equivalents of an inorganic hydrogen halide (preferably hydrogen chloride, hydrogen bromide and hydrogen fluoride) or with a halogenated alkyl carboxylic acid of 1–4 carbons, preferably trifluoroacetic acid. The reaction is run in anhydrous hydrogen fluoride, or, when employing other acids, in an optional inert solvent.

Typical solvents include alkyl carboxylic acids of 1–3 carbons, such as acetic acid and the like; ethers such as diethyl ether, dioxane, tetrahydrofuran and the like; alkanols of 1–6 carbons such as methanol, ethanol, and the like; alkyl esters wherein both the acid and the alcohol from which the ester is derived may have from 1–4 carbon atoms such as ethyl acetate, propyl acetate, ethyl propionate and the like; halogenated hydrocarbons such as methylene chloride, chloroform, di-, tri- and tetrachloroethanes and the like; nitroalkanes of 1–4 carbons such as nitromethane, nitroethane and the like; or alkyl ketones having alkyl radicals of 1–4 carbons such as acetone, methylethyl ketone and the like.

The reaction is carried out at from about −50° C. to about 200° C., preferably from about 0° C. to about 120° C., until a significant amount of end product is obtained, typically, for from about 1/10 to about 92, preferably from about 1/6 to about 30 hours. The product is isolated by conventional techniques. For example, with all acids except hydrogen fluoride, the reaction mixture is diluted with an inert water-immiscible organic solvent, washed with dilute aqueous sodium bicarbonate, dried and chromatographed. When using hydrogen fluoride, the hydrogen fluoride is evaporated, the residue dissolved in an inert organic solvent, such as halogenated hydrocarbons, e.g., methylene chloride, chloroform or trichloroethylene; alkyl esters wherein both the acid and the alcohol from which the ester is derived may have from 1–4 carbon atoms, e.g., ethyl acetate, propyl acetate, ethyl propionate and the like, washed with water, dried and chromatographed.

The compounds of formula V wherein $R_1^1$ and/or $R_1^2$ are ZCOOH and $R^4$ and $R^5$ are other than alkanoyl, and/or $R^4$ and/or $R^5$ are OH are also obtained by selectively hydrolyzing compounds of formula V, wherein $R_1^1$ and/or $R_1^2$ are $ZCO_2R^9$, and/or $R^4$ and/or $R^5$ are

(1–3 carbons) with from about 0.2 to about 6, preferably about 0.8 to about 3, molar equivalents of an alkali metal (preferably sodium and potassium) hydroxide, bicarbonate or carbonate in an optional inert organic solvent, in optional presence of water. Depending on the particular compound, care must be taken to minimize hydrolysis and cleavage of the quinazoline ring. Preferred conditions include absolute ethanolic potassium hydroxide. Suitable organic solvents include lower molecular weight alcohols, such as methanol, ethanol and the like; water-miscible ethers, such as tetrahydrofuran, 1,2-dimethoxyethane, dioxane and the like; N,N-dialkylformamides, N,N-dialkyl alkanoylamides wherein the alkyl and alkanoyl radicals have 1–4 carbons, such as dimethylformamide, dimethylacetamide, and the like. The reaction is carried out at from about −50° C. to about 200° C., preferably about −20° C. to about 70° C., for from about ¼ to about 72 hours, preferably about ½ to about 24 hours. The products are isolated in a conventional manner. For example, the reaction mixture is neutralized with acetic acid, evaporated and chromatographed.

Compounds of formula I wherein $R^4$ and/or $R^5$ are lower alkoxy are also prepared by reacting compounds of formula I wherein $R^4$ and/or $R^5$ are hydroxyl and where $R^3 \neq H$ or, if $R^3 = H$, the product may have $R^3$ = lower alkyl group of $R^4$ and/or $R^5$, with from about 0.5 to about 12, preferably from about 0.8 to about 3.0 molar equivalents of an appropriate base, e.g., $KHCO_3$, followed by reaction of the thus formed salt with a corresponding molar equivalent of an appropriate alkylating agent of formula lower alkyl-M wherein M is any group which is compatible with alkyl (1–3 carbons), and capable of being displaced by aryloxide anion under the reaction conditions. Some typical M groups include halogen, preferably chlorine, bromine, iodine;

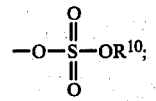

or an alkyl or arylsulfonate of formula

wherein $R^{10}$ can be alkyl of 1-6 carbons or aryl of from about 6 to 10 carbons optionally substituted by halogen, nitro or alkyl of 1-3 carbons. The reaction is run in an essentially inert organic solvent, e.g., lower alkyl ketones, such as methyl ethyl ketone.

Other typical bases include alkali metals (preferably lithium, sodium and potassium) and their salts of alkanols of 1-6 carbons such as methanol, ethanol, i-propanol, t-butyl alcohol, n-amyl alcohol and the like; of ammonia; of mono- and dialkylamines wherein the alkyl groups contain from 1-6 carbons such as ethylamine, diethylamine, diisopropylamine, cyclohexyl isopropylamine and the like; of acidic hydrocarbons such as triphenylmethane and the chromatography of the crude reaction extract. On the other hand, the corresponding product where $R^6$=lower alkyl can be obtained by employing other conditions such as using a large excess of the alkylating agent, elevated reaction temperatures and/or increased reaction times.

Compounds of formula V, wherein one of $R_1^1$ and $R_1^2$ is H but $R_1^1 \neq H$ when $R_1^2 = CO_2H$ are also prepared by decarboxylating compounds of formula V wherein one of $R^1$ and $R^2$ is carboxy in conventional manner, e.g., heating in the optional presence of a catalyst and/or organic solvent. Typical catalysts include: copper metal and salts, e.g., cuprous chloride. Typical solvents are: pyridine, butidine, quinoline, quinaldine; high-boiling ethers, e.g., diphenyl ether, di- and triethylene glycol ethers.

The reaction is carried out from 50° C. (or the freezing point of the run mixture) to 400° C. (or the reflux temperature) for from 0.2 hour to 48 hours, or until the reaction is essentially complete.

Compounds of formula I wherein $R^4$ and $R^5$ are other than OH and $R^3$ is other than hydrogen or optionally substituted phenyl are also prepared by reacting compounds of formula I wherein $R^3$ is hydrogen with from about 0.5 to about 2, preferably from about 0.8 to about 1.3 molar equivalents of an appropriate base, followed by reaction of the thus formed salt with a corresponding molar equivalent of an appropriate alkylating agent of formula $R^3$-M wherein $R^3$ is other than hydrogen or optionally substituted phenyl and M is any group which is compatible with $R^3$ and capable of being displaced by the salt under the reaction conditions. Some typical M groups include halogen, preferably chlorine, bromine, iodine;

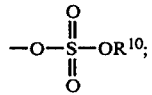

or an alkyl or arylsulfonate of formula

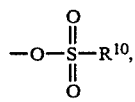

where $R^{10}$ can be alkyl of 1-6 carbons or aryl of from about 6 to 10 carbons optionally substituted by halogen, nitro or alkyl of 1-3 carbons. The reaction is run in an essentially inert organic solvent.

Typical bases include alkali metals (preferably lithium, sodium and potassium) and their salts of alkanols of 1-6 carbons such as methanol, ethanol, i-propanol, t-butyl alcohol, n-amyl alcohol and the like; of ammonia; of mono- and dialkylamines wherein the alkyl groups contain from 1-6 carbons such as ethylamine, diethylamine, diisopropylamine, cyclohexyl isopropylamine and the like; of acidic hydrocarbons such as triphenylmethane and the like; thallous salts of the preceding alkanols, and, preferably, alkali metal hydrides such as sodium hydride.

Typical organic solvents include alkanols of 1-5 carbons such as methanol, ethanol, t-butyl alcohol, n-butanol and the like; ethers of 4-12 carbons such as tetrahydrofuran, dioxane, diphenyl ether, 1,2-dimethoxyethane and the like; N,N-dialkylformamides, N,N-dialkylalkanoylamides wherein the alkyl and alkanoyl radicals have 1-4 carbons, such as dimethylformamide, dimethylacetamide and the like; dialkyl sulfoxides, hexamethylphosphorous triamide and their mixtures.

The reaction is carried out at from about $-20°$ C. to about 300° C., preferably from about 0° C. to about 100° C. for from about 0.2 hour to about 96 hours, preferably from about 0.5 hour to about 72 hours.

The products are isolated by conventional techniques. For example, the reaction mixture is evaporated; the residue is neutralized with aqueous acid, extracted with a water-immiscible, inert solvent such as methylene chloride, washed with water, dried and chromatographed.

In the above reaction when $R^6$=H in the starting material, selective conditions must be employed to minimize alkylation of the hydroxyl at the 2-position so that $R^6$=H in the product. On the other hand, by using an excess of the alkylating agent, the corresponding product where $R^6$=lower alkyl can be obtained.

Compounds of formula V wherein $R^1_1$ and/or $R^2_1$ is Z—$OR^6$, where $R^6$ is lower alkanoyl, aralkanoyl, optionally substituted benzoyl are also prepared by reacting compounds of formula I wherein $R^1$ and/or $R^2$ is Z—$OR^6$ and $R^6$ is hydrogen with from about 0.8 to about 6, preferably from about 1 to about 3, molar equivalents of acyl derivatives of formula

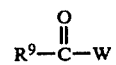

(where W is halogen, preferably chlorine and bromine, hydroxy, a radical of formula

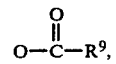

or a radical of formula

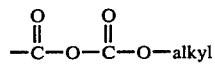

wherein alkyl has 1-6 carbons), in the optional presence of an appropriate base, in an optional, essentially inert organic solvent.

Typical suitable bases include heterocyclic amines of 5-10 carbons such as pyridine, 2-methylpyridine, 2,6-dimethylpyridine, quinoline, quinaldine and the like; trialkylamines wherein the alkyl radicals have 1-5 carbons, such as triethylamine, tributylamine and the like.

Typical inert organic solvents which may be used include aryl hydrocarbons such as benzene, toluene, xylene and the like; di-, tri- and tetra- chlorinated hydrocarbons such as trichloro and methylene chloride, chloroform, dichloro-, and tetrachloroethanes and the like; ethers such as 1,2-dimethoxyethane, tetrahydrofuran, dioxane and the like; N,N-dialkylformamides and alkyl alkanoylamides wherein the alkyl and alkanoyl radicals have 1-4 carbons such as dimethylformamide, dimethylacetamide and the like. In the preferred method, where W is hydroxy, no solvent is necessary and the reaction is carried out at the reflux temperature of the starting mixture, if liquid, or at the fusion point, if the starting mixture is a solid.

The reaction is carried out at from about 0° C. to about reflux, preferably from about 20° C. to about reflux, until a significant amount of end product is obtained, typically, for from 0.5 to about 80 hours, preferably from about 1 to about 24 hours.

The product is isolated by conventional techniques. For example, the reaction mixture is evaporated and diluted with a water-imiscible organic solvent such as chlorinated hydrocarbons, e.g., methylene chloride or chloroform and the like. The organic solution is washed with water, dried and chromatographed. In the above reaction when $R^4$ and/or $R^5$=OH in the starting materials, varying amount of another product wherein $R^4$ and/or $R^5$ is the same, lower alkanoyl, aralkanoyl, optionally substituted benzoyl may be obtained.

It will be appreciated that the compounds of formula V described above may be converted to the formula I compounds of the invention as described hereinbefore.

Starting materials or final products that are mixtures of isomers can be separated into the single isomers by methods in themselves known, e.g., by fractional distillation crystallization and/or chromatography. Racemic products can likewise be resolved into the optical antipodes, for example, by separation of diastereomeric salts thereof, e.g., of the fractional crystallization, in the case of basic compounds, of d- or l-tartrates, maleates, -mandelates, -N-acetylphenylalaninates or -camphor sulfonates, or, in the case of acid compounds, d- or l-α-methylbenzylamine and reconverting the diastereomeric salts into the free antipodes.

Certain of the compounds of formula I may form physiologically acceptable acid-addition salts or base addition salts with inorganic and organic acids or alkali metal or alkaline earth metal bases such as sodium hydroxide or calcium hydroxide. These salts frequently provide useful means for isolating the products from reaction mixtures by forming the salt in a medium in which it is insoluble. The free base may then be obtained by neutralization, e.g., with a base or acid. Then any other salts may again be formed from the free base and the appropriate inorganic acid or base. Illustrative are the hydrohalides, especially the hydrochloride and hydrobromide which are preferred, sulfate, nitrate, phosphate, oxalate, tartrate, maleate, fumarate, citrate, succinate, methanesulfonate, benzenesulfonate, toluenesulfonate, and the like.

The compounds of formula I, and their pharmaceutically acceptable salts, are useful in treating various allergic conditions in mammalian species such as mice, cats, dogs, etc., when administered in amounts ranging from about 1 milligram to about 500 milligrams per kilogram of body weight per day. The compounds can be used prophylactically or therapeutically to treat various allergic and immunological disorders and in particular to treat certain type of asthma, hay-fever, and rhinitis. A preferred dosage regimen would be from about 3 milligrams to about 200 milligrams per kilogram of body weight per day administered in a single dose or plurality of divided doses.

The compounds of formula I, and the pharmaceutically acceptable salts thereof, are anti-allergics which inhibit the effects of certain antigen-antibody reaction and in particular inhibit the release of mediators such as histamine. The anti-allergy activity of these compounds is determined by the reaginic antibody-induced passive cutaneous anaphylaxis (PCA) reaction in rats. (See Bach, Immediate Hypersensitivity: Laboratory Models and Experimental Findings, Ann. Rep. Med. Chem., 7: 238-248 (1972), for a discussion of the predictability of clinical efficacy of compounds active in the PCA).

A compound of formula I, or a salt thereof, can be administered by the inhalation of an aerosol or powder as described in U.S. Pat. No. 3,772,336 (i.e., breathing finely divided particles of the active ingredient into the lungs), orally, or parenterally. Powders can be prepared by comminuting the active ingredient with a similarly comminuted diluent such as starch or lactose. Suitable forms for oral administration include capsules, tablets, and syrups, and a suitable form for parenteral administration is a sterile injectable. Such unit dosage forms are prepared by compounding with a conventional vehicle, excipients, binders, preservatives, stabilizers, flavoring agents or the like as called for by acceptable pharmaceutical practice. Also, the compounds of this invention can be formulated with other pharmaceutically active compounds such as bronchodilators, steroids, antihistamines, etc.

The compounds of the invention are also useful as antiinflammatory agents as determined by the reverse passive arthus test [Agents & Actions, 5, 39 (1975)] and are effective in the prevention and inhibition of granuloma formation in warm blooded animals, and may be used, for example, in a manner similar to phenylbutazone or indomethacin. They may be used to decrease joint swelling, tenderness, pain and stiffness in mammalian species, such as dogs and monkeys, e.g., in conditions such as rheumatoid arthritis.

Furthermore, the compounds of the invention are useful in mammals as inhibitors of 3',5'-cyclic adenosine phosphodiesterase and 3',5'-cyclic guanosine phosphodiesterase, as well as anxiolytic agents at a dosage level of from about 12 to about 100 mg/kg per day ip in one dose or in up to 4 divided doses; as inhibitors of platelet aggregation in vitro and therefore of potential use in the treatment of thrombosis.

The compounds of the present invention in the described dosages may be administered orally; however, other routes such as intraperitoneally, subcutaneously, intramuscularly or intravenously may be employed.

The active compounds of the present invention are orally administered, for example, with an inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suspensions, syrups, wafers, chewing gum, and the like. The amount of active compound in such therapeutically useful compositions or preparations is such that a suitable dosage will be obtained.

The tablets, troches, pills, capsules and the like may also contain the following; a binder such as gum tragacanth, acacia, corn starch or gelatin; an excipient such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain in addition to materials of the above type a liquid carrier such as a fatty oil. Various other materials may be present as coatings or to otherwise modify the physical form of the dosage unit, for instance, tablets, pills or capsules may be coated with shellac, sugar, or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

The following Examples further illustrate and represent preferred embodiments of the invention. All temperatures are expressed in degrees Centigrade.

EXAMPLE 1

5,6-Dihydro-5-oxopyrazolo[1,5-c]quinazoline-2-carboxamide

A. Propiolamide

Methyl propiolate (50 g; 0.59 mole) is added dropwise to 250 ml of liquid ammonia at −60°. After keeping the reaction mixture at this temperature for 15–20 hours, ammonia is allowed to evaporate off at room temperature. Yield: 51 g. A portion dried on a porous plate gives a white solid, m.p. 57°–58°.

B. 5,6-Dihydro-5-oxopyrazolo[1,5-c]quinazoline-2-carboxamide 4.8 g (0.03 mole) of 3-diazooxindole and 2.4 g (0.035 mole) of the propiolamide are taken up in benzene (250 ml) and refluxed overnight under a stream of nitrogen. The light tan precipitates that form are filtered off and dried in a vacuum oven for 4 hours. Yield: 4.4 g. Additional refluxing of the filtrate gives 900 mg of product. Total yield: 5.3 g (77.4%).

The crude product is recrystallized from dimethylformamide (200 ml) and water (300 ml). White solid is obtained which is dried for 24 hours in a vacuum oven at 100°. Yield: 4.4 g, m.p. 355°–358°.

Anal. Calcd for $C_{11}H_8N_4O_2$: C, 57.89; H, 3.53; N, 24.55. Found: C, 57.63; H, 3.70, N. 24.24.

EXAMPLE 1a

2-[[[(Phenylamino)carbonyl]oxy]methyl]-pyrazolo[1,5-c]-quinazolin-5(6H)-one 2.0 g (0.0093 mole) of 2-(hydroxymethyl)-pyrazolo[1,5-c]-quinazolin-5(6H)-one prepared as described in Example 6B and 1.55 ml (≅1.7 g or 0.014 mole) of 98% phenylisocyanate are refluxed in 20 ml of dry pyridine under $N_2$ for 1 hour. The crude product is poured onto 200 ml of ice-water layered with ethyl acetate (50 ml) and stirred for 30 minutes. The precipitates that form are filtered off, air-dried and taken up in dioxane (150 ml). The solution is filtered while hot and the clear filtrate concentrated down to a volume of 100 ml and cooled. The precipitates are filtered off and dried in vacuo at 85°. Yield 2.45 g, 78.8% crude yield.

The product is recrystallized once more from dioxane (600 ml), concentrating the clear solution down to a volume of 150 ml and cooled. The precipitates are filtered off and dried in vacuo for 3 days at 115°. Yield: 1.9 g, m.p. 282°–283°.

EXAMPLE 2

5,6-Dihydro-5-oxopyrazolo[1,5-c]quinazoline-2-carbonitrile

A. Cyanoacetylene 4.0 g (0.058 mole) of propiolamide is mixed in a flask with 13.0 g of phosphorus pentoxide and heated slowly in an oil bath up to 200° under a distillation column. (The cyanoacetylene starts distilling over at a bath temperature of ∼80°, so the oil bath is kept at ∼100° over a period of time until distillation slows down at which point the temperature is slowly raised to 200°). Yield: 2.2 g, b.p 40°–42°. Percent yield=79%.

B. 5,6-Dihydro-5-oxopyrazolo[1,5-c]quinazoline-2-carbonitrile 6.0 g (0.04 mole) of 3-diazooxindole and 2.2 g (0.045 mole) of cyanoacetylene are taken up in benzene (250 ml) and refluxed overnight under $N_2$. The mixture is cooled and the beige-colored precipitates are filtered off. The crude product is dried in a vacuum oven at room temperature for 3 hours. Yield: 5.2 g, m.p. 302°–304°. Percent yield: 65.6.

The crude product obtained is recrystallized by taking it up in methanol (700 ml) and chloroform (200 ml) and concentrating the solution down to a volume of 400 ml. After cooling, the precipitate is filtered off and dried overnight in a vacuum oven at ∼100°. Yield: 4.0 g; m.p. 317°–320°.

Anal. Calcd for $C_{11}H_6N_4O$: C, 62.86; H, 2.88; N, 26.65. Found: C, 62.70; H, 2.90; N, 26.54.

EXAMPLE 3

2-[2-(4-Morpholinyl)-2-thioxoethyl]pyrazolo[1,5-c]quinazolin-5(6H)-one 4.0 g (0.018 mole) of 2-acetylpyrazolo[1,5-c]quinazolin-5(6$\underline{H}$)-one, 1.41 g sulfur and 3.1 g of morpholine are mixed well and heated in an oil bath at 150° for 3 hours. The mixture is cooled and the solid obtained is washed successively with water (50 ml), 6 $\underline{N}$ HCl (50 ml) and water (150 ml). The solid material is then taken up in 1.4 liters absolute ethanol and 300 ml of chloroform, heated to boiling until a clear solution is obtained and treated with activated carbon for ∼10 minutes. The suspension is filtered through a celite pad, while washing the pad well with 100 ml boiling ethanol. The filtrate is then concentrated down to a volume of ∼800 ml, cooled; the light yellow precipitates that form are filtered off and dried in a vacuum oven at 60° C. for 2½ hours to give 3.8 g of product, m.p. 273°–275°. Percent yield: 67.1% (recrystallized).

EXAMPLE 4

2-(1H-Tetrazol-5-yl)pyrazolo[1,5-c]quinazolin-5(6$\underline{H}$)-one 1.6 g (0.0076 mole) of 5,6-dihydro-5-oxopyrazolo[1,5-c]quinazoline-2-carbonitrile (prepared as described in Example 2), 546 mg of sodium azide (0.0084 mole or 1.1 equivalent) and 449 mg (1.1 equivalent) of ammonium chloride are suspended in dimethylformamide (30 ml) and the mixture is heated at 100° under $N_2$ for 29 hours with stirring. The reaction mixture is cooled and stripped to dryness. The crude product is suspended in water (75 ml) and treated with concentrated HCl (1.5 ml) to pH 2. The mixture is stirred for ∼15 minutes and filtered; the precipitates obtained are washed well with water and air-dried to yield: 2.17 g, quantitative crude yield, m.p. 287°-289°.

The crude product is triturated with boiling dioxane (50 ml) and the light beige precipitates obtained are taken up in methanol (1.4 liters) and chloroform (300 ml). The hot solution is filtered and the clear filtrate concentrated down to a volume of ~600 ml. The solution is cooled to yield: 1.76 g.

The product obtained is taken up in hot dimethylformamide (50 ml), filtered while hot and the clear filtrate is cooled down and diluted with water. The precipitates obtained are filtered off, re-suspended in water (75 ml) and boiled for 18 10 minutes. The precipitates are then cooled and filtered and dried in a vacuum oven at 70° over $P_2O_5$ for 20 hours. Yield: 1.24 g, m.p. 292°-294°.

Anal. Calcd $C_{11}H_7N_7O$: C, 52.18; H, 2.79; H, 38.72. Found: C, 51.89; H, 2.58, N, 38.45.

EXAMPLE 5

5,6-Dihydro-5-oxopyrazolo[1,5-c]quinazoline-2-carboxylic acid, 3-(dimethylamino)propyl ester, hydrochloride (1:1)

A. 5,6-Dihydro-5-oxopyrazolo[1,5-c]quinazoline-2-carboxylic acid, sodium salt 5,6-Dihydro-5-oxopyrazolo[1,5-c]quinazoline-2-carboxylic acid (4.58 g, 0.02 mole) is suspended in 300 ml of water and treated with 1.68 g (0.02 mole) of solid sodium bicarbonate. The mixture is stirred for 0.05 hour during which time almost complete solution results. The water is stripped to a low volume and 400 ml of acetone added. The white solid is filtered, washed with acetone and then ether to give 4.8 g of product.

B. 5,6-Dihydro-5-oxopyrazolo[1,5-c]quinazoline-2-carbonyl chloride 4.8 g (0.019 mole) of 5,6-dihydro-5-oxopyrazolo[1,5-c]-quinazoline-2-carboxylic acid, sodium salt is added to a solution of 3.27 g (0.026 mole) of oxalyl chloride in 200 ml of benzene. The suspension is stirred at room temperature for 20 minutes and then refluxed under nitrogen for 2 hours. The solvent is stripped to give the product.

C. 5,6-Dihydro-5-oxopyrazolo[1,5-c]quinazoline-2-carboxylic acid, 3-(dimethylamino)propyl ester, hydrochloride (1:1)

The acid chloride of part B is suspended in 200 ml of pyridine under nitrogen, a solution of 1.98 g (0.019 mole) of dimethylaminopropanol slowly is added dropwise, and the reaction mixture is stirred overnight at room temperature.

The resulting solid is filtered, triturated with water and refiltered, weight 3.7 g (51% direct yield). The solid is extracted with hot 1 normal aqueous hydrochloric acid and insoluble material (1.5 g, which proves to be the product) filtered while hot. The filtrate is concentrated to crystals in vacuo. The crystals are filtered and dried (675 mg). An analytical sample is prepared by recrystallization from methanol-ethyl acetate (4:1), 550 mg, m.p. 202°-204°.

Anal. Calcd for $C_{16}H_{18}N_4O_3 \cdot H_2O \cdot HCl$: C, 52.11; H, 5.74; N, 15.19; Cl, 9.61. Found: C, 51.88; H, 5.95; N, 15.09; Cl, 9.48.

EXAMPLE 6

2-[[(Chloroacetyl)oxy]methyl]pyrazolo-[1,5-c]quinazolin-5(6H)-one

A. 5,6-Dihydro-5-oxopyrazolo[1,5-c]quinazoline-2-carboxylic acid, ethyl ester

A solution of 48 g (0.30 mole) of 3-diazooxindole and 38.7 g (0.39 mol) of ethyl propiolate in 2 l. of benzene is refluxed overnight. The reaction mixture is cooled to room temperature and the crude product filtered, wt.=60 g. Crystallization from absolute ethanol gives 54 g, m.p. 242°-244° (Sl. d.).

An analytical sample is prepared by taking a 10 g aliquot of the above material and recrystallizing three times with absolute ethanol, m.p. 253°-254° (Sl. d.), 3.9 g.

B. 2-(Hydroxymethyl)pyrazolo[1,5-c]quinazolin-5(6H)-one

A suspension of 3.84 g (0.015 mole) of 5,6-dihydro5-oxopyrazolo[1,5-c]quinazoline-2-carboxylic acid ethyl ester prepared as described in part A above is stirred in 150 ml of tetrahydrofuran under nitrogen at room temperature. There is added 24 ml (0.034 mole) of a 20% solution of diisobutyl aluminum hydride in hexane. The resultant solution is stirred for 1 hour at room temperature whereupon 50 ml of methanol is added and the reaction mixture refluxed for 1 hour. The precipitate of aluminum alkoxide is filtered, air dried and Soxhlet extracted for 48 hours with boiling methanol. The extract is combined with the above filtrate and stripped to give 3.2 g of a white solid (quantitative yield). Recrystallization from methanol gives 2.7 g of pure title compound, m.p. 285°-287°.

C. 2-[[(Chloroacetyl)oxy]methyl]pyrazolo[1,5-c]-quinazolin-5(6H)-one

A mixture of 6.0 g (0.028 mole) of compound of part B and 60 g of monochloroacetic acid are heated at the point of fusion in a silicone oil bath (bath temperature 60°-65°) for six hours under nitrogen, employing a magnetic stirrer for agitation. After five hours reaction time, a very thick solid precipitates from the clean melt. The reaction mixture is cooled to room temperature, extracted with water and the solid filtered (7.3 g, 90% yield).

An analytical sample is prepared by recrystallization of 2.0 g of the above material from methylethyl ketone to give 1.4 g, m.p. 244°-246° (dec.).

Anal. Calcd for $C_{13}H_{10}N_2O_3Cl$: C, 53.53; H, 3.44; N, 14.41; Cl, 12.20 Found: C, 53.73; H, 3.25; N, 14.51; Cl, 12.38.

EXAMPLE 7

2-[2-(1-Piperidinyl)ethyl]pyrazolo[1,5-c]quinazolin-5(6)-one

A. 5,6-Dihydro-5-oxopyrazolo[1,5-c]quinazoline-2-acetic acid 4.0 g (0.012 mole) of 2-[2-(4-morpholinyl)-2-thioxoethyl]1,5-c]-quinazolin-5(6H)-one (prepared as described in Example 3), is refluxed in concentrated hydrochloric acid (80 ml) for 4 hours and cooled. The pecipitates are filtered off, washed well with water and dried in a vacuum oven at 80° for 3 hours. Yield: 2.84 g, 96% crude yield. The crude product is taken up in methanol (1.1 liters) and chloroform (300 ml), heated to boiling and the clear solution treated with activated carbon for ~10 minutes. The hot suspension is filtered through a celite pad and the clear filtrate concentrated down to a volume of ~400 ml on the steam bath and cooled. The light yellow precipitates are filtered off and dried in a vacuum oven at 60° C. for 4 hours. Yield: 1.97 g, m.p. 253°-254°.

B. 2-(2-Hydroxyethyl)pyrazolo[1,5-c]quinazolin-5-(6H)-one 2.0 g (0.082 mole) of 5,6-dihydro-5-oxopyrazolo[1,5-c]-quinazoline-2-acetic acid is taken up in distilled tetrahydrofuran (50 ml) and treated dropwise with 1 M $BH_3$ (0.011 mol or 1.3 equivalents) at 0°. The mixture is stirred for 2 hours at room temperature and stripped to dryness. The solid is suspended in 50 ml $H_2O$, treated dropwise with 1 N HCl (20 ml) and stirred for 45 minutes. The product obtained (800 mg) is redissolved in THF (20 ml) and treated with 15 ml of 1 M $BH_3$. The mixture is then stirred at room temperature for 3 days.

The resulting suspension is treated with 1 N HCl (~5 ml), stirred for 30 minutes and stripped to dryness. The crude product is then chromatographed on a preparative silica gel plate and the desired band extracted successively with methylene chloride and methanol. Yield: 500 mg. This product is dried three times over $P_2O_5$ at elevated temperatures in a vacuum oven until a constant value of the compound with ¼ mole $H_2O$ is obtained.

C. 2-[2-[[(4-Methylphenyl)sulfonyl]oxy]ethyl]-pyrazolo-[1,5-c]quinazolin-5(6H)-one 12.0 g (0.052 mole) of 2-(2-hydroxyethyl)-pyrazolo[1,5-c]quinazolin-5-(6H)-one is taken up in pyridine (120 ml), cooled down to 0° and treated with 11.0 g (0.058 mole or 1.1 equivalent) of 98% tosyl chloride. The mixture is stirred for 4 hours, keeping the temperature below 20° during the reaction period, after which it is poured onto 1.8 l. of ice-water and stirred until solids form. The off-white precipitates are filtered off and dried in vacuo at 100° for 3 hours. Yield: 17.43 g, m.p. 194°-196°; 87.4% crude yield.

The crude product is taken up in hot dioxane (450 ml) and the clear solution obtained is concentrated down to a volume of 100 ml. The solution is cooled and cream-colored precipitates form which are filtered off and dried over the weekend in vacuo at 90°. Yield: 13.63 g, m.p. 203°-205°.

Anal. Calcd for $C_{19}H_{17}N_3O_4S$: C, 59.52; H, 4.47; N, 10.96; S, 8.36. Found: C, 59.25; H. 4.32; N, 10.72; S, 8.25.

D. 2-[2-(1-Piperidinyl)ethyl]pyrazolo[1,5-c]quinazolin-5(6H)-one, hydrochloride (1:1)

2.0 g (0.0052 mole) of 2-[2-[[(4-methylphenyl)sulfonyl]oxy]ethyl]pyrazolo[1,5-c]quinazolin-5-(6H)-one and 2.0 ml of freshly distilled piperidine (or 5 equivalents), are taken up in methanol (10 ml) and the reaction mixture is refluxed for another hour. The solvent is then stripped off and the syrup obtained azeotroped 2 times with benzene. The syrup is then triturated with water (10 ml) and the solid that forms is filtered off and dried overnight in vacuo at 70°. Yield: 1.3 g, m.p. 188°-190°; 84.4% crude yield.

The crude product is combined with another batch (~300 gm) made previously and taken up in 35 ml absolute ethanol. The solution is treated with 1.08 ml of 7 N HCl/EtOh, stirred for 30-45 minutes and stripped to dryness. The crude salt which forms is taken up in 200 ml absolute ethanol, treated with activated carbon while hot and filtered through a celite pad, washing the pad with a small amount of hot absolute EtOH. The washings and filtrate are combined, concentrated down to a volume of ~30 ml and cooled. The precipitates obtained (1.48 g) are recrystallized again from the same amount of ethanol. The product obtained is then dried in vacuo over $P_2O_5$ at 95° for 24 hours. Yield: 1.29 g, m.p. 280°-281°.

Anal. Calcd for $C_{17}H_{20}N_4O$: C, 61.35; H, 6.36; N, 16.83; Cl, 10.65. Found: C, 61.32; H, 6.37; N, 16.60; Cl, 10.73.

EXAMPLE 8

4-Methyl-1-piperazineacetic acid, (5,6-dihydro-5-oxo-pyrazolo[1,5-c]quinazolin-2-yl)methyl ester, hydrochloride (1:1)

2.0 g (0.0069 mol) of 2-[[(chloroacetyl)oxy]methyl]-pyrazolo[1,5-c]-quinazoline-5-(6H)-one prepared as described in Example 6 and 1.0 ml (≃0.885 g of 1.28 equivalent) of 98% N-methylpiperazine are refluxed in 350 ml of dimethoxyethane under $N_2$ for 22 hours. The reaction mixture is cooled and the solid that forms is filtered off. Yield: 2.12 g, m.p. 246°-248°, 78.5% crude yield.

The crude product is taken up in a mixture of absolute ethanol (300 ml) and methylene chloride (125 ml), filtered while hot and the clear filtrate concentrated down to a volume of ~75 ml. The solution is cooled, the precipitates that form are precipitated off and dried in vacuo at 85° overnight, followed by another drying period of 24 hours in vacuo at 100° over $P_2O_5$. Yield: 1.01 g, m.p. 247°-249°.

Anal Calcd for $C_{18}H_{21}N_5O_8$. HCl: C, 55.17; H, 5.66; N, 17.87; Cl, 9.05. Found: C, 54.90; H, 5.47; N, 17.59; Cl, 9.19.

EXAMPLE 9

2-[1-[(Aminocarbonyl)oxy]ethyl]-6-methyl-pyrazolo[1,5-c]quinazolin-5(6H)-one

A. 2-Acetyl-6-methylpyrazolo[1,5-c]quinazolin-5(6H)-one

To a solution of 5.0 g (0.0288 mole) of 1-methyl-3-diazooxindole in 200 ml of benzene there is added 2.38 g (0.035 mole) of 3-butyn-2-one and the solution refluxed overnight.

The reaction mixture is cooled to room temperature and the crude product filtered off and washed with ether to give 4.5 g, m.p. 250°-251°. Recrystallization from chloroform/methanol gives 4.0 g of pure product, m.p. 250°-251°.

B. 2-(1-Hydroxyethyl)-6-methylpyrazolo[1,5-c]quinazoline-5(6H)-one 6.4 g (0.02669 mole) of 2-acetyl-6-methyl-pyrazolo[1,5-c[quinazolin-5(6H)-one is suspended in 325 ml of methanol and chilled in an ice bath. Thereto is added (portions) 4.85 g (0.128 mole) of sodium borohydride. The mixture is stirred for 15 minutes in the ice bath, during which time a clear solution forms; the solution is stirred for 30 minutes at room temperature.

The solution is treated with 100 ml of water and the methanol stripped. The aqueous solution is extracted three time each with 100 ml of dichloromethane. The combined organic phases are washed twice with 75 ml each of saturated sodium chloride solution, dried with anhydrous sodium sulfate, and stripped to a foamy residue of 6.5 g (quantitative yield). This is covered with pentane and allowed to stand overnight at 5°. The tacky solid that forms is filtered and dissolved in boiling acetone. Concentration of the solution on the steam bath and filtration on cooling gives 4.4 g of analytically pure title compound, m.p. 169°-172°.

Anal. Calcd for $C_{13}H_{13}N_3O_2$: C, 64.19; H, 5.39; N, 17.27. Found: C, 64.03; H, 5.53; N, 17.46.

C. 2-[1-[(Aminocarbonyl)oxy]ethyl]-6-methyl-pyrazolo[1,5-c]quinazolin-5(6H)-one

To a suspension of 3.7 g (0.0172 mole) of 2-(1-hydroxyethyl)-6-methylpyrazolo[1,5-c]quinazolin-5(6H)-one in 30 ml of benzene there is added 2.6 g (0.036 mole) of solid, 90% sodium cyanate followed by the dropwise addition of 3.1 ml (0.041 mole) of trifluoroacetic acid. The reaction mixture is stirred on a magnetic stirrer at approximately 120 revolutions per minute for 2 hours at room temperature. By the end of this time a gum separates. The reaction mixture is subsequently treated with 15 ml of water with increased stirring speed after which a solid (insoluble in either phase) forms. This is filtered, washed with water and air dried to give 2.9 g (60% direct yield), m.p. 216°–221°. The solid is twice crystallized from chloroform-methanol (1:1) to give 2.0 g of analytically pure material, m.p. 250°–252°.

Anal. Calcd for $C_{14}H_{14}N_4O_3$: C, 58.75; H, 4.93; N, 19.57. Found: C, 58.83, H, 5.06; N, 19.71.

EXAMPLES 10 to 46

Following the procedure of Example 1, but substituting the compounds indicated in Column I of Table I below for diazooxindole and the compounds indicated in Column II below for propiolamide in Example 1, the compounds indicated in Column III are obtained.

TABLE I

| Ex. No. | Column I $R^4$ (position) | $R^5$ (position) | $R^1$ | Column II Z | Column III $R^4$ | $R^5$ | $R^1$ | Z |
|---|---|---|---|---|---|---|---|---|
| 10. | s-$C_4H_9$(5) | H | H | —$(CH_2)_2$— | s-$C_4H_9$(9) | H | As per Column II | |
| 11. | $CH_3$(7) | $CH_3$(6) | $CH_3$ | $CH_2$ | $CH_3$(7) | $CH_3$(8) | | |
| 12. | n-$C_3H_7$(6) | H | n-$C_4H_9$C(O)—$CH_2$— | $CH_2$ | n-$C_3H_7$(8) | H | | |
| 13. | $CH_3$(5) | $CH_3$(6) | H | —CH($CH_3$)— | $CH_3$(9) | $CH_3$(8) | | |
| 14. | $C_2H_5$(4) | H | H | —$CH_2$CH($C_2H_5$)— | $C_2H_5$(10) | H | | |
| 15. | $CH_3O$(4) | H | H | $CH_2$ | $CH_3O$(10) | H | | |
| 16. | $C_2H_5O$(5) | H | $CH_3C(O)$— | —$CH_2$—C($CH_3$)—$CH_2$— | $C_2H_5O$(9) | H | | |
| 17. | $CH_3O$(4) | H | $CH_3$ | —$CH_2$— | $CH_3O$(10) | H | | |
| 18. | $CH_3O$(5) | OH(6) | H | —CH($CH_3$)—$(CH_2)_2$— | $CH_3O$(9) | OH(8) | | |
| 19. | OH(5) | $OCH_3$(7) | H | —$(CH_2)_2$— | OH(9) | $OCH_3$(7) | | |
| 20. | OH(5) | H | $C_2H_5$ | —$(CH_2)_3$— | OH(9) | H | | |
| 21. | $CH_3O$(5) | H | $CH_3C(O)$ | —$CH_2$— | $CH_3O$(9) | H | | |
| 22. | Ph—$CH_2$—O—(5) | H | $C_2H_5C(O)$ | —C($CH_3)_2$— | Ph—$CH_2O$(9) | H | | |
| 23. | Br(5) | H | H | —$CH_2$— | Br(9) | H | | |
| 24. | Cl(4) | $CH_3$(7) | H | —$CH_2$— | Cl(10) | $CH_3$(7) | | |
| 25. | Cl(6) | H | H | —$(CH_2)_2$— | Cl(8) | H | | |
| 26. | $CF_3$(7) | H | $CH_3$ | —$CH_2$— | $CF_3$(7) | H | | |
| 27. | $CF_3$(5) | $CF_3$(6) | $CH_3$ | —$CH_2$—CH($C_2H_5$)— | $CF_3$(9) | $CF_3$(8) | | |
| 28. | F(5) | H | $CH_3$—Ph—C(O)—$CH_2$ | —$CH_2$— | F(9) | H | | |
| 29. | H | H | H | —$CH_2$—CH($C_2H_5$)—$CH_2$— | H | H | | |
| 30. | H | H | HC(O)—$(CH_2)_3$ | —$(CH_2)_3$— | H | H | | |
| 31. | H | H | $CH_3$ | — | H | H | | |
| 32. | H | H | H | — | H | H | | |
| 33. | $CH_3CO$(4) | H | H | — | $CH_3C(O)$(10) | H | | |
| 34. | $CH_3$(4) | $CH_3O$(5) | H | — | $CH_3$(10) | $CH_3O$(9) | | |

TABLE I-continued

| | Column I | | | | Column III | | | |
|---|---|---|---|---|---|---|---|---|
| Ex. No. | $R^4$ (position) | $R^5$ (position) | $R^1$ | Z | $R^4$ | $R^5$ | $R^1$ | Z |
| 35. | $C_2H_5(5)$ | $C_2H_5(6)$ | H | — | $C_2H_5(9)$ | $C_2H_5(8)$ | | |
| 36. | $CH_3O(4)$ | H | H | — | $CH_3O(10)$ | H | | |
| 37. | $CH_3O(4)$ | H | H | — | $CH_3O(10)$ | H | | |
| 38. | $CH_3O(4)$ | H | $CH_3$ | — | $CH_3O(10)$ | H | | |
| 39. | $CH_3O(5)$ | H | $CH_3$ | — | $CH_3O(9)$ | H | | |
| 40. | $CH_3O(5)$ | H | H | — | $CH_3O(9)$ | H | | |
| 41. | $CH_3O(5)$ | H | $CH_3$ | — | $CH_3O(9)$ | H | | |
| 42. | $CH_3O(7)$ | H | H | — | $CH_3O(7)$ | H | | |
| 43. | $CH_3O(7)$ | Cl(4) | H | — | $CH_3O(7)$ | Cl(10) | | |
| 44. | H | H | H | — | H | H | | |
| 45. | H | H | $C_2H_5$ | — | H | H | | |
| 46. | F(5) | H | H | — | F(9) | H | | |

EXAMPLES 47 TO 83

Following the procedures of Example 2, but substituting the compounds indicated in Column I of Table II below for diazooxindole and the compounds indicated in Column II below for propiolamide in Example 2, the compounds indicated in Column III are obtained.

TABLE II

| Ex. No. | $R^4$ | $R^5$ | $R^3$ | $R^1$ | $R^4$ | $R^5$ | $R^3$ | $R^1$ |
|---|---|---|---|---|---|---|---|---|
| 47 | H | H | $CH_3$ | H | H | H | as per column I | as per column II |
| 48 | H | H | $C_2H_5$ | H | H | H | | |
| 49 | H | H | $i\text{-}C_3H_7$ | $CH_3$ | H | H | | |
| 50 | H | H | $CH_2\text{-}\langle\text{C}_6H_4\rangle\text{-}Cl$ | H | H | H | | |
| 51 | H | H | $\langle\text{C}_6H_4\rangle\text{-}OCH_3$ | H | H | H | | |
| 52 | $CH_3O(7)$ | H | $CH_3$ | H | $CH_3O(7)$ | H | | |
| 53 | $CH_3O(6)$ | H | $n\text{-}C_4H_9$ | H | $CH_3O(8)$ | H | | |
| 54 | $CH_3O(6)$ | H | $CH_3$ | H | $CH_3O(8)$ | H | | |
| 55 | $CH_3O(5)$ | H | $CH_3$ | H | $CH_3O(9)$ | H | | |
| 56. | $CH_3O(4)$ | H | $CH_3$ | H | $CH_3O(10)$ | H | | |
| 57. | $CH_3O(4)$ | H | $s\text{-}C_4H_9$ | H | $CH_3O(10)$ | H | | |
| 58. | $CH_3O(4)$ | H | $CH_2\text{-}\langle\text{C}_6H_5\rangle$ | H | $CH_3O(10)$ | H | | |
| 59. | $CH_3O(5)$ | H | $CH_2\text{-}\langle\text{C}_6H_4\rangle\text{-}Cl$ | $CH_3$ | $CH_3O(9)$ | H | | |
| 60. | $i\text{-}C_4H_9(6)$ | H | $n\text{-}C_3H_7$ | $C_2H_5$ | $i\text{-}C_4H_9(8)$ | H | | |
| 61. | $CH_3(4)$ | H | $CH_3$ | H | $CH_3(10)$ | H | | |
| 62. | $CH_3(4)$ | H | $\langle\text{C}_6H_4\rangle\text{-}CF_3$ | H | $CH_3(10)$ | H | | |
| 63. | F(5) | H | $CH_3$ | H | F(9) | H | | |

TABLE II-continued

| | Column I | | | Column II | Column III | | | |
|---|---|---|---|---|---|---|---|---|
| Ex. No. | $R^4$ | $R^5$ | $R^3$ | $R^1$ | $R^4$ | $R^5$ | $R^3$ | $R^1$ |
| 64. | Cl(4) | CH$_3$O(7) | CH$_2$-C$_6$H$_4$-Cl | CH$_3$ | Cl(10) | CH$_3$O(7) | | |
| 65. | CF$_3$(7) | H | C$_2$H$_5$ | H | CF$_3$(7) | H | | |
| 66. | CH$_3$CO(5) | H | CH$_3$ | H | CH$_3$CO(9) | H | | |
| 67. | C$_6$H$_5$-CH$_2$O(6) | H | i-C$_3$H$_7$ | H | C$_6$H$_5$-CH$_2$O(8) | H | | |
| 68. | C$_2$H$_5$(5) | C$_2$H$_5$(6) | CH$_2$-C$_6$H$_4$-OCH$_3$ | CH$_3$ | C$_2$H$_5$(9) | C$_2$H$_5$(8) | | |
| 69. | H | H | CH$_3$ | HOCH$_2$— | H | H | | |
| 70. | H | H | i-C$_3$H$_7$ | HOC(C$_2$H$_5$)(CH$_3$)— | H | H | | |
| 71. | H | H | CH$_2$-C$_6$H$_5$ | HOCH$_2$ | H | H | | |
| 72. | H | H | CH$_2$-C$_6$H$_4$-Cl | HO(CH$_2$)$_2$— | H | H | | |
| 73. | H | H | CH$_2$-C$_6$H$_4$-CF$_3$ | HO(CH$_2$)$_4$— | H | H | | |
| 74. | CH$_3$(5) | H | CH$_3$ | HOCH(n-C$_3$H$_7$)— | CH$_3$(9) | H | | |
| 75. | n-C$_3$H$_7$(5) | n-C$_3$H$_7$(6) | C$_2$H$_5$ | HOCH$_2$ | n-C$_3$H$_7$(9) | n-C$_3$H$_7$(8) | | |
| 76. | CH$_3$O(4) | H | CH$_3$ | HOCH$_2$ | CH$_3$O(10) | H | | |
| 77. | CH$_3$O(4) | H | CH$_3$ | HOCH$_2$ | CH$_3$O(10) | H | | |
| 78. | CH$_3$O(4) | H | CH$_3$ | HOCH$_2$ | CH$_3$O(10) | H | | |
| 79. | s-C$_4$H$_9$(5) | H | CH$_2$-C$_6$H$_5$ | HO(CH$_2$)$_2$ | s-C$_4$H$_9$(9) | H | | |
| 80. | CH$_3$CO(6) | H | C$_6$H$_5$ | HOCH-C$_6$H$_5$ | CH$_3$CO(8) | H | | |
| 81. | Cl(4) | CH$_3$(7) | i-C$_4$H$_9$ | HO(CH$_2$)$_3$ | Cl(10) | CH$_3$(7) | | |
| 82. | F(6) | H | C$_2$H$_5$ | HOCH$_2$CHCH$_2$—CH$_3$ | F(8) | H | | |
| 83. | CF$_3$(7) | H | CH$_2$-C$_6$H$_4$-OCH$_3$ | HOCH$_2$ | CF$_3$(7) | H | | |

EXAMPLES 84 TO 104

Following the procedure of Example 3, but substituting the compounds indicated in Column I, Table II below for acetylpyrazolo[1,5-c]quinazolin-5(6H)-one, the compounds indicated in Column II are obtained.

TABLE III

| | Column I | | | | Column II | | | |
|---|---|---|---|---|---|---|---|---|
| Ex. No. | $R^4$ (position) | $R^5$ (position) | $R^1$ | Z | $R^4$ (position) | $R^5$ (position) | $R^1$ | Z |
| 84. | H | H | $CH_3$ | $-CH_2-$ | as in Column I | | | |
| 85. | H | H | H | $-(CH_2)_2-$ | | | | |
| 86. | H | H | H | $-(CH_2)_3-$ | | | | |
| 87. | $CH_3(10)$ | H | H | $-CH_2-$ | | | | |
| 88. | H | H | H | $-CH(CH_3)-$ | | | | |
| 89. | $CH_3O(10)$ | H | H | $-CH_2-$ | | | | |
| 90. | $CH_3O(10)$ | H | H | $-CH(CH_3)CH_2CH_3 \text{ (branch)}$ — actually $-CH(CH_3)-$ with $-CH_2-CH_3$ | | | | |
| 91. | $CH_3(10)$ | H | H | $-CH_2-$ | | | | |
| 92. | $C_2H_5O(9)$ | H | $CH_3$ | $-CH_2-CH(CH_3)-$ | | | | |
| 93. | H | H | H | $-CH_2-C(CH_3)_2-CH_2-$ | | | | |
| 94. | $CH_3O(5)$ | H | $CH_3$ | $-CH_2-$ | | | | |
| 95. | $CH_3O(7)$ | H | H | $-CH_2-$ | | | | |
| 96. | H | H | H | cyclohexyl | | | | |
| 97. | F(9) | H | H | $-CH(C_2H_5)-$ | | | | |
| 98. | $CH_3(9)$ | H | $C_2H_5$ | $-CH_2-CH(CH_3)-$ | | | | |
| 99. | $CH_3(8)$ | $CH_3(9)$ | H | cyclohexyl | | | | |
| 100. | $CF_3(7)$ | H | $CH_3$ | cyclohexyl | | | | |
| 101. | $NH_2$ | H | H | $-CH_2-$ | | | | |
| 102. | H | H | $CH_3$ | $-(CH_2)_3-$ | | | | |
| 103. | H | H | $CH_3$ | $-CH(CH_3)-CH_2-$ | | | | |
| 104. | H | H | H | $-CH(phenyl)-$ | | | | |

Note: Example 90 Z = $-CH(CH_3)-$ attached $-CH_2-CH_3$ (i.e. sec-butyl-like linker).

EXAMPLES 105 TO 141

Following the procedure of Example 4, but substituting the compounds indicated in Column I of Table IV below for the 5,6-dihydro-5-oxopyrazolo[1,5-c]quinazoline-2-carbonitrile (which are prepared in Examples 47 to 83, respectively), the compounds indicated in Column III are obtained.

TABLE IV

| | Column I | Column II |
|---|---|---|

| Ex. No. | R⁴ | R⁵ | R³ | R¹ | R⁴ R⁵ R³ R¹ |
|---|---|---|---|---|---|
| 105. | H | H | $CH_3$ | H | as per column I |
| 106. | H | H | $C_2H_5$ | H | |
| 107. | H | H | $i$-$C_3H_7$ | $CH_3$ | |
| 108. | H | H | $CH_2$-(4-Cl-phenyl) | H | |
| 109. | H | H | (4-$OCH_3$-phenyl) | H | |
| 110. | $CH_3O(7)$ | H | $CH_3$ | H | |
| 111. | $CH_3O(8)$ | H | $n$-$C_4H_9$ | H | |
| 112. | $CH_3O(8)$ | H | $CH_3$ | H | |
| 113. | $CH_3O(9)$ | H | $CH_3$ | H | |
| 114. | $CH_3O(10)$ | H | $CH_3$ | H | |
| 115. | $CH_3O(10)$ | H | $s$-$C_4H_9$ | H | |
| 116. | $CH_3O(10)$ | H | $CH_2$-phenyl | H | |
| 117. | $CH_3O(9)$ | H | $CH_2$-(4-Cl-phenyl) | $CH_3$ | |
| 118. | $i$-$C_4H_9(8)$ | H | $n$-$C_3H_7$ | $C_2H_5$ | |
| 119. | $CH_3(10)$ | H | $CH_3$ | H | |
| 120. | $CH_3(10)$ | H | $CH_2$-(3-$CF_3$-phenyl) | H | |
| 121. | F(9) | H | $CH_3$ | H | |
| 122. | Cl(10) | $CH_3O(7)$ | $CH_2$-(4-Cl-phenyl) | $CH_3$ | |
| 123. | $CF_3(10)$ | H | $C_2H_5$ | H | |
| 124. | $CH_3CO(9)$ (C=O) | H | $CH_3$ | H | |
| 125. | phenyl-$CH_2O(8)$ | H | $i$-$C_3H_7$ | H | |
| 126. | $C_2H_5(9)$ | $C_2H_5(8)$ | $CH_2$-(4-$OCH_3$-phenyl) | $CH_3$ | |
| 127. | H | H | $CH_3$ | $HOCH_2$ | |
| 128. | H | H | $i$-$C_3H_7$ | $HOC(C_2H_5)(CH_3)$ | |
| 129. | H | H | $CH_2$-phenyl | $HOCH_2$ | |
| 130. | H | H | $CH_2$-(4-Cl-phenyl) | $HO(CH_2)_2$ | |
| 131. | H | H | $CH_2$-(3-$CF_3$-phenyl) | $HO(CH_2)_4$ | |
| 132. | $CH_3(9)$ | H | $CH_3$ | $HOCH$-$n$-$C_3H_7$ | |
| 133. | $n$-$C_3H_7(9)$ | N—$C_3H_7(8)$ | $C_2H_5$ | $HOCH_2$ | |
| 134. | $CH_3O(10)$ | H | $CH_3$ | $HOCH_2$ | |
| 135. | $CH_3O(10)$ | H | $CH_3$ | $HOCH_2$ | |

TABLE IV-continued

| | Column I | | | | Column II | | | |
|---|---|---|---|---|---|---|---|---|
| Ex. No. | R⁴ | R⁵ | R³ | R¹ | R⁴ | R⁵ | R³ | R¹ |
| 136. | $CH_3O(10)$ | H | $CH_3$ | $HOCH_2$ | | | | |
| 137. | $s\text{-}C_4H_9(9)$ | H | $CH_2\text{-}\phi$ | $HO(CH_2)_2$ | | | | |
| 138. | $CH_3CO(8)$ (C=O) | H | $\phi$ | $HOCH\text{-}\phi$ | | | | |
| 139. | $Cl(10)$ | $CH_3(7)$ | $i\text{-}C_4H_9$ | $HO(CH_2)_3$ | | | | |
| 140. | $F(8)$ | H | $C_2H_5$ | $HOCH_2CHCH_2\text{-}$ with $CH_3$ | | | | |
| 141. | $CF_3(7)$ | H | $CH_2\text{-}\phi\text{-}OCH_3$ | $HOCH_2$ | | | | |

EXAMPLES 142 TO 182

Following the procedure of Example 5, but substituting for 5,6-dihydro-5-oxopyrazolo[1,5-c]quinazoline-2-carboxylic acid the compound shown in column I of Table V below and substituting for dimethylaminopropanol the compound shown in column II below, and the compound of the invention shown in Column III is obtained.

TABLE V

| | Column I | | | Column II | | Column III | | |
|---|---|---|---|---|---|---|---|---|
| | R¹ ... COOH structure | | | $HO\text{-}Z\text{-}N(R_1)(R_2)$ | | R¹ ... $C(=O)\text{-}O\text{-}Z\text{-}N(R_1)(R_2)$ structure | | |
| Ex. No. | R⁴ (position) | R⁵ (position) | z | R₁ | R₂ | R⁴ (position) | R⁵ (position) | R₁ R₂ z |
| 142. | $t\text{-}C_4H_9(5)$ | H | $-(CH_2)_2-$ | H | $s\text{-}C_5H_{11}$ | $t\text{-}C_4H_9(9)$ | H | as in column II |
| 143. | $CH_3(7)$ | $CH_3(6)$ | $-CH_2-$ | $CH_3$ | $n\text{-}C_{10}H_{21}$ | $CH_3(7)$ | $CH_3(8)$ | |
| 144. | $i\text{-}C_3H_7(5)$ | H | $-CH_2-$ | $n\text{-}C_4H_9$ | $n\text{-}C_4H_9$ | $i\text{-}C_3H_7(9)$ | H | |
| 145. | $CH_3(5)$ | $CH_3(6)$ | $-CH(CH_3)-$ | H | $CH_3$ | $CH_3(9)$ | $CH_3(8)$ | |
| 146. | $C_2H_5(4)$ | H | $-CH_2CH(C_2H_5)-$ | H | $CH_2\text{-}\phi$ | $C_2H_5(10)$ | H | |
| 147. | $CH_3O(4)$ | H | $-CH_2-$ | H | $CH_3$ | $CH_3O(10)$ | H | |
| 148. | $C_2H_5O(5)$ | H | $-CH_2-C(CH_3)-CH_2-$ | $CH_3$ | $CH_3$ | $C_2H_5O(9)$ | H | |
| 149. | $CH_3O(4)$ | H | $-CH_2$ | $CH_3$ | $s\text{-}C_5H_{11}$ | $CH_3O(10)$ | H | |
| 150. | $OH(5)$ | $OH(6)$ | $-CH(CH_3)-(CH_2)_2-$ | H | $CH_3$ | $OH(9)$ | $OH(8)$ | |
| 151. | $OH(5)$ | $OCH_3(7)$ | $-(CH_2)_2-$ | H | $C_2H_5$ | $OH(9)$ | $OCH_3(7)$ | |
| 152. | $OH(5)$ | H | $-(CH_2)_3-$ | $C_2H_5$ | $CH_2\text{-}\phi\text{-}CH_3$ | $OH(9)$ | H | |
| 153. | $CH_3O(5)$ | H | $-CH_2-$ | $CH_3$ | $CH_3$ | $CH_3O(9)$ | H | |
| 154. | $\phi\text{-}CH_2\text{-}O(5)$ | H | $-C(CH_3)(CH_2)-$ | $C_2H_5$ | $C_2H_5$ | $\phi\text{-}CH_2\text{-}O(9)$ | H | |
| 155. | $Br(5)$ | H | $-CH_2-$ | H | $n\text{-}C_6H_{13}$ | $Br(9)$ | H | |

TABLE V-continued

| | Column I | | | | | Column III | | | | |
|---|---|---|---|---|---|---|---|---|---|---|
| |  | | | HO—Z—N(R₁)(R₂) | |  | | | | |
| Ex. No. | R⁴ (position) | R⁵ (position) | z | R₁ | R₂ | R⁴ (position) | R⁵ (position) | R₁ | R₂ | z |
| 156. | Cl(4) | CH₃(7) | —CH₂— | H | CH₂— | Cl(10) | CH₃(7) | | | |
| 157. | Cl(6) | H | —(CH₂)— | CH₃ | s-C₄H₉ | Cl(8) | H | | | |
| 158. | CF₃(7) | H | —CH₂— | CH₃ | CH₃ | CF₃(7) | H | | | |
| 159. | CF₃(5) | CF₃(5) | —CH₂—CH(C₂H₅)— | CH₃ | CH₃ | CF₃(9) | CF₃(8) | | | |
| 160. | F(5) | H | —CH₂— | C₂H₅ | C₂H₅ | F(9) | H | | | |
| 161. | H | H | —CH₂—CH(C₂H₅)—CH₂— | H | CH₃ | H | H | | | |
| 162. | H | H | —(CH₂)₃— | H | CH₃ | H | H | | | |
| 163. | t-C₄H₉(5) | H | — | H | n-C₅H₁₁ | t-C₄H₉(9) | H | | | |
| 164. | CH₃(7) | CH₃(6) | — | CH₃ | n-C₁₀H₂₁ | CH₃(7) | CH₃(8) | | | |
| 165. | i-C₃H₇(6) | H | — | s-C₄H₉ | s-C₄H₉ | i-C₃H₇(8) | H | | | |
| 166. | CH₃(5) | CH₃(6) | — | H | CH₃ | CH₃(9) | H | | | |
| 167. | C₂H₅(4) | H | — | H | CH₂— | C₄H₉(10) | H | | | |
| 168. | CH₃O(4) | H | — | H | CH₃ | CH₃O(10) | H | | | |
| 169. | C₂H₅O(5) | H | — | CH₃ | CH₃ | C₂H₅O(9) | H | | | |
| 170. | CH₃O(4) | H | — | CH₃ | n-C₄H₉ | CH₃O(10) | H | | | |
| 171. | CH₂OH(5) | OH(6) | — | H | CH₃ | CH₂OH(9) | OH(8) | | | |
| 172. | OH(6) | OCH₃(7) | — | H | C₂H₅ | OH(8) | OCH₃(7) | | | |
| 173. | OH(5) | H | — | C₂H₅ | CH₂——CH₃ | OH(9) | H | | | |
| 174. | CH₃O(5) | H | — | CH₃ | CH₃ | CH₃O(9) | H | | | |
| 175. | —CH₂—O(5) | H | — | C₂H₅ | C₂H₅ | —CH₂—O(9) | H | | | |
| 176. | Br(5) | H | — | H | n-C₆H₁₃ | Br(9) | H | | | |
| 177. | Cl(4) | CH₃(7) | — | H | CH₂—⌬ | Cl(10) | CH₃(7) | | | |
| 178. | Cl(5) | H | — | H | n-C₄H₉ | Cl(9) | H | | | |
| 179. | CF₃(7) | H | — | H | CH₃ | CF₃(7) | H | | | |
| 180. | CF₃(5) | CF₃(6) | — | CH₃ | ⌬ | CF₃(9) | CF₃(8) | | | |
| 181. | F(5) | H | — | CH₃ | CH₃ | F(9) | H | | | |
| 182. | H | H | — | CH₃ | CH₃ | H | H | | | |

EXAMPLES 183 TO 204

Following the procedure of Example 6, but substituting the compounds indicated in Column I, Table VI below for 2-(hydroxymethyl)pyrazolo[1,5-c]quinazolin-5(6H)-one (prepared as described in application Ser. No. 702,364 filed Aug. 6, 1976 and incorporated herein reference), the acids indicated in Column II below for monochloro acetic acid in Example 6, the compounds indicated in Column III are obtained.

TABLE VI

| | Column I | | | | Column II | Column III | | | | |
|---|---|---|---|---|---|---|---|---|---|---|
| Ex. No. | R⁴ (position) | R⁵ (position) | R¹ | z | HOCR⁶ (R⁶) | R⁴ (position) | R⁵ (position) | R¹ | z | R⁶ |
| 183. | H | H | CH₃ | —CH₂— | CH₂Cl | | | | | |

TABLE VI-continued

| | Column I | | | | | Column II | Column III | | | | | |
|---|---|---|---|---|---|---|---|---|---|---|---|---|
| Ex. No. | R⁴ (position) | R⁵ (position) | $R^1$ | z | $R^6$ | $HOCR^6$ | R⁴ (position) | R⁵ (position) | $R^1$ | z | $R^6$ | |
| 184. | H | H | H | —(CH$_2$)$_2$— | CH$_2$Br | | as in Column I | | | | as in Column II | |
| 185. | H | H | H | —(CH$_2$)$_3$— | C$_2$H$_4$Cl | | | | | | | |
| 186. | CH$_3$(10) | H | H | —CH$_2$— | C$_3$H$_6$Cl | | | | | | | |
| 187. | H | H | H | —CH(CH$_3$)— | CH$_2$Cl | | | | | | | |
| 188. | CH$_3$O(10) | H | H | —CH$_2$— | C$_2$H$_4$Br | | | | | | | |
| 189. | CH$_3$O(10) | H | H | —CH(CH$_3$)— (with CH$_2$—CH$_3$) | C$_4$H$_8$Cl | | | | | | | |
| 190. | CH$_3$O(10) | H | H | —CH$_2$— | CH$_2$Cl | | | | | | | |
| 193. | C$_2$H$_5$O(9) | H | CH$_3$ | —CH$_2$—CH(CH$_3$)— | CH$_2$Cl | | | | | | | |
| 194. | H | H | H | —CH$_2$—C(CH$_3$)(CH$_3$)—CH$_2$— | C$_2$H$_4$Cl | | | | | | | |
| 193. | CH$_3$O(5) | H | CH$_3$ | —CH$_2$— | CH$_2$Cl | | | | | | | |
| 194. | CH$_3$O(7) | H | H | —CH$_2$— | C$_4$H$_8$Cl | | | | | | | |
| 195. | H | H | H | (cyclohexylidene) | CH$_2$Cl | | | | | | | |
| 196. | F(9) | H | H | —CH(C$_2$H$_5$)— | C$_2$H$_4$Br | | | | | | | |
| 197. | CH$_3$(9) | H | C$_2$H$_5$ | —CH$_2$—CH(CH$_3$)— | C$_4$H$_8$Cl | | | | | | | |
| 198. | CH$_3$(8) | CH$_3$(9) | H | (spiro cyclopentane) | C$_2$H$_4$Cl | | | | | | | |
| 199. | CF$_3$(7) | H | CH$_3$ | (spiro cyclohexane) | CH$_2$Cl | | | | | | | |
| 200. | NH$_2$ | H | H | —CH$_2$— | C$_3$H$_6$Cl | | | | | | | |
| 201. | H | H | CH$_3$ | —(CH$_2$)$_3$— | C$_4$H$_8$Br | | | | | | | |
| 202. | H | H | CH$_3$ | —CH(CH$_3$)—CH$_2$— | CH$_2$Cl | | | | | | | |
| 203. | H | H | H | —CH(C$_6$H$_5$)— | CH$_2$Cl | | | | | | | |

EXAMPLES 204A TO 224

Following the procedure of Example 8, but substituting the compounds indicated in Column I, Table VII below for 2-[[(chloroacetyl)oxy]methyl]pyrazolo[1,5-c]quinazolin-5(6H)-one and the compounds indicated in Column II below for N-methylpiperazine in Example 8, the compounds indicated in Column III are obtained.

TABLE VII

Column I

TABLE VII-continued

| Ex. No. | R⁴ (position) | R⁵ (position) | $R^1$ | z | $R^6$ |
|---|---|---|---|---|---|
| 204a. | H | H | CH$_3$ | —CH$_2$— | CH$_2$Cl |
| 205. | H | H | H | —(CH$_2$)$_2$— | CH$_2$Br |
| 206. | H | H | H | —(CH$_2$)$_3$— | C$_2$H$_4$Cl |

TABLE VII-continued

| | | | | | |
|---|---|---|---|---|---|
| 207. | CH₃(10) | H | H | —CH₂— | C₃H₆Cl |
| 208. | H | H | H | —CH(CH₃)— | CH₂Cl |
| 209. | CH₃O(10) | H | H | —CH₂— | C₂H₄Br |
| 210. | CH₃O(10) | H | H | —CH(CH₃)CH₂CH₃— | C₄H₈Cl |
| 211. | CH₃O(10) | H | H | —CH₂— | CH₂Cl |
| 212. | C₂H₅O(9) | H | CH₃ | —CH₂—CH(CH₃)— | CH₂Cl |
| 213. | H | H | H | —CH₂—C(CH₃)(CH₃)—CH₂— | C₂H₄Cl |
| 214. | CH₃O(5) | H | CH₃ | —CH₂— | CH₂Cl |
| 215. | CH₃O(7) | H | H | —CH₂— | C₄H₈Cl |
| 216. | H | H | H | cyclohexylidene | CH₂Cl |
| 217. | F(9) | H | H | —CH(C₂H₅)— | C₂H₄Br |
| 218. | CH₃(9) | H | C₂H₅ | —CH₂—CH(CH₃)— | C₄H₈Cl |
| 219. | CH₃(8) | CH₃(9) | H | cyclobutylidene | C₂H₄Cl |
| 220. | CF₃(7) | H | CH₃ | cyclohexylidene | CH₂Cl |
| 221. | NH₂ | H | H | —CH₂— | C₃H₆Cl |
| 222. | H | H | CH₃ | —(CH₂)₃— | C₄H₈Br |
| 223. | H | H | CH₃ | —CH(CH₃)CH₂— | CH₂Cl |
| 224. | H | H | H | —CH(C₆H₅)— | CH₂Cl |

Column II

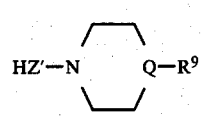

| Ex. No. | Z' | Q—R⁹ |
|---|---|---|
| 204a. | —CH₂— | N—CH₃ |
| 205. | —CH₂— | N—C₂H₅ |
| 206. | —(CH₂)₂— | N—C₃H₇ |
| 207. | —(CH₂)₃— | N—C₄H₉ |
| 208. | —CH(CH₃)— | N—C₅H₁₁ |
| 209. | —CH(CH₃)CH₃— | N—CH₃ |
| 210. | —CH₂— | CH—CH₃ |
| 211. | —(CH₂)₂— | CH—C₂H₅ |
| 212. | —CH₂— | CH—C₃H₇ |
| 213. | —CH₂— | CH—CH₃ |
| 214. | —(CH₂)₂— | N—CH₃ |
| 215. | —(CH₂)₃— | N—C₂H₅ |
| 216. | —CH₂— | N—CH₃ |
| 217. | —CH₂— | N—i-C₃H₇ |
| 218. | —(CH₂)₃— | N—t-C₄H₉ |
| 219. | —CH₂— | N—CH₃ |
| 220. | —(CH₂)₂— | CH—CH₃ |
| 221. | —CH₂— | CH—C₂H₅ |
| 222. | —CH₂— | CH—CH₃ |
| 223. | —CH₂— | N—CH₃ |
| 224. | —(CH₂)₂— | N—C₂H₅ |

Column III

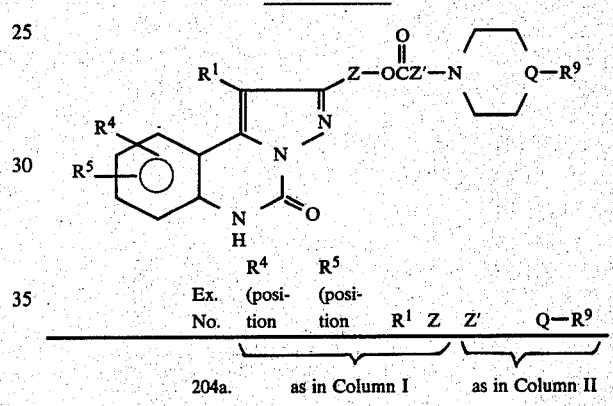

| Ex. No. | R⁴ (position) | R⁵ (position) | R¹ | Z | Z' | Q—R⁹ |
|---|---|---|---|---|---|---|
| 204a. | as in Column I | | | | as in Column II | |
| 205. | | | | | | |
| 206. | | | | | | |
| 207. | | | | | | |
| 208. | | | | | | |
| 209. | | | | | | |
| 210. | | | | | | |
| 211. | | | | | | |
| 212. | | | | | | |
| 213. | | | | | | |
| 214. | | | | | | |
| 215. | | | | | | |
| 216. | | | | | | |
| 217. | | | | | | |
| 218. | | | | | | |
| 219. | | | | | | |
| 220. | | | | | | |
| 221. | | | | | | |
| 222. | | | | | | |
| 223. | | | | | | |
| 224. | | | | | | |

EXAMPLES 225 TO 245

Following the procedure of Example 9, but substituting the compounds indicated in Column I, Table VIII below for 2-(hydroxymethyl)pyrazolo[1,5-c]quinazolin-5(6H)-one, the compounds indicated in Column II are obtained.

TABLE VIII

| | Column I | | | | | Column II | | | | |
|---|---|---|---|---|---|---|---|---|---|---|
| Ex. No. | R⁴ (position) | R⁵ (position) | $R^1$ | Z | $R^3$ | R⁴ (position) | R⁵ (position) | $R^1$ | Z | $R^3$ |
| 225. | H | H | $CH_3$ | $-CH_2-$ | $CH_3$ | | | | | |
| 226. | H | H | H | $-(CH_2)_2-$ | H | | | as in Column I | | |
| 227. | H | H | H | $-(CH_2)_3-$ | $C_2H_5$ | | | | | |
| 228. | $CH_3(10)$ | H | H | $-CH_2-$ | $n-C_3H_7$ | | | | | |
| 229. | H | H | H | $-CH(CH_3)-$ | $CH_3$ | | | | | |
| 230. | $CH_3O(10)$ | H | H | $-CH_2-$ | $C_2H_5$ | | | | | |
| 231. | $CH_3O(10)$ | H | H | $-CH(CH_3)CH_2CH_3-$ | $s-C_4H_9$ | | | | | |
| 232. | $CH_3O(10)$ | H | H | $-CH_2-$ | $-CH_2-C_6H_5$ | | | | | |
| 233. | $C_2H_5O(9)$ | H | $CH_3$ | $-CH_2-CH(CH_3)-$ | $C_6H_5$ | | | | | |
| 234. | H | H | H | $-CH_2-C(CH_3)_2-CH_2-$ | $-CH_2-C_6H_4-CH_3$ | | | | | |
| 235. | $CH_3O(5)$ | H | $CH_3$ | $-CH_2-$ | H | | | | | |
| 236. | $CH_3O(7)$ | H | H | $-CH_2-$ | $n-C_4H_9$ | | | | | |
| 237. | H | H | H | cyclohexyl | $CH_3$ | | | | | |
| 238. | F(9) | H | H | $-CH(C_2H_5)-$ | $C_2H_5$ | | | | | |
| 239. | $CH_3(9)$ | H | $C_2H_5$ | $-CH_2-CH(CH_3)-$ | $i-C_4H_9$ | | | | | |
| 240. | $CH_3(8)$ | $CH_3(9)$ | H | cyclohexyl | H | | | | | |
| 241. | $CF_3(7)$ | H | $CH_3$ | cyclohexyl | $CH_3$ | | | | | |
| 242. | $NH_2$ | H | H | $-CH_2-$ | $i-C_3H_7$ | | | | | |
| 243. | H | H | $CH_3$ | $-(CH_2)_3-$ | $s-C_4H_9$ | | | | | |
| 244. | H | H | $CH_3$ | $-CH(CH_3)-CH_2-$ | $CH_3$ | | | | | |
| 245. | H | H | H | $-CH(C_6H_5)-$ | $CH_3$ | | | | | |

EXAMPLES 246 TO 266

Disubstituted amino-derivatives of the Examples 225 to 245 compounds are prepared by dialkylating the Examples 225 to 245 compounds indicated in Column I, Table IX below with the alkyl bromide indicated in Column II below in the presence of sodium hydride, to form the dialkylated compounds indicated in Column III.

TABLE IX

Column I:

$$R^1 \text{ pyrazolo-quinazoline with } Z-C(=O)-NH_2, R^4, R^5, R^3$$

Column II: $R_xBr$

Column III:

$$R^1 \text{ pyrazolo-quinazoline with } Z-OC(=O)N(R_x)_2$$

| Ex. No. | $R^4$ (position) | $R^5$ (position) | $R^1$ | Z | $R^3$ | $R_x$ | $R^4$ (position) | $R^5$ (position) | $R^1$ | Z | $R^3$ | $R_x$ |
|---|---|---|---|---|---|---|---|---|---|---|---|---|
| 246. | H | H | $CH_3$ | $-CH_2-$ | $CH_3$ | $CH_3$ | as in Column I | | | | | As in Column II |
| 247. | H | H | H | $-(CH_2)_2-$ | H | $C_2H_5$ | | | | | | |
| 248. | H | H | H | $-(CH_2)_3-$ | $C_2H_5$ | $C_3H_7$ | | | | | | |
| 249. | $CH_3(10)$ | H | H | $-CH_2-$ | $n\text{-}C_3H_7$ | $C_4H_9$ | | | | | | |
| 250. | H | H | H | $-CH(CH_3)-$ | $CH_3$ | $CH_3$ | | | | | | |
| 251. | $CH_3O(10)$ | H | H | $-CH_2-$ | $C_2H_5$ | $CH_3$ | | | | | | |
| 252. | $CH_3O(10)$ | H | H | $-CH(CH_3)_2$ (isopropyl —CH—) | $s\text{-}C_4H_9$ | $C_2H_5$ | | | | | | |
| 253. | $CH_3O(10)$ | H | H | $-CH_2-$ | $-CH_2-C_6H_5$ | $CH_3$ | | | | | | |
| 254. | $C_2H_5O(9)$ | H | $CH_3$ | $-CH_2-CH(CH_3)-$ | $-C_6H_5$ | $CH_3$ | | | | | | |
| 255. | H | H | H | $-CH_2-C(CH_3)_2-CH_2-$ | $-CH_2-(3\text{-}CH_3\text{-}C_6H_4)$ | $C_2H_5$ | | | | | | |
| 256. | $CH_3O(5)$ | H | $CH_3$ | $-CH_2-$ | H | $CH_3$ | | | | | | |
| 257. | $CH_3O(7)$ | H | H | $-CH_2-$ | $n\text{-}C_4H_9$ | $CH_3$ | | | | | | |
| 258. | H | H | H | cyclohexylidene | $CH_3$ | $C_2H_5$ | | | | | | |
| 259. | F(9) | H | H | $-CH(C_2H_5)-$ | $C_2H_5$ | $CH_3$ | | | | | | |
| 260. | $CH_3(9)$ | H | $C_2H_5$ | $-CH_2-CH(CH_3)-$ | $i\text{-}C_4H_9$ | $CH_3$ | | | | | | |
| 261. | $CH_3(8)$ | $CH_3(9)$ | H | cyclopropylidene | H | $C_2H_5$ | | | | | | |
| 262. | $CF_3(7)$ | H | $CH_3$ | cyclohexylidene | $CH_3$ | $CH_3$ | | | | | | |
| 263. | $NH_2$ | H | H | $-CH_2-$ | $i\text{-}C_3H_7$ | $C_2H_5$ | | | | | | |
| 264. | H | H | $CH_3$ | $-(CH_2)_3-$ | $s\text{-}C_4H_9$ | $CH_3$ | | | | | | |
| 265. | H | H | $CH_3$ | $-CH(CH_3)-CH_2-$ | $CH_3$ | $CH_3$ | | | | | | |
| 266. | H | H | H | $-CH(C_6H_5)-$ | $CH_3$ | $CH_3$ | | | | | | |

What is claimed is:

1. A compound of the structure

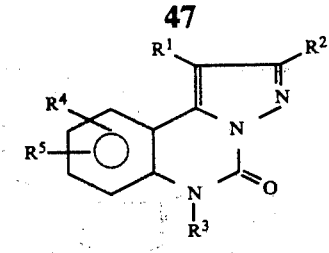

wherein R¹ represents hydrogen, lower alkyl, phenyl optionally substituted with R⁴, R² is cyano; or

wherein Z is a single bond or

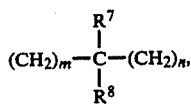

X is O or S);

R³ is hydrogen, lower alkyl, benzyl or phenyl optionally substituted by an R⁴ radical as defined below;

R⁴ and R⁵ may be the same or different and are hydrogen, lower alkyl, lower alkoxy, hydroxy, lower alkanoyloxy,

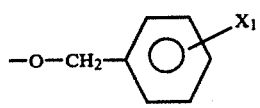

($X_1$ is hydrogen, lower alkoxy, or $NO_2$);

R⁷ and R⁸ may be the same or different and represent hydrogen, lower alkyl, phenyl optionally substituted with $X_1$ or benzyl optionally substituted with $X_1$, $(CH_2)_m$ and $(CH_2)_n$ represent a single bond or straight or branched chain alkylene radicals; and m and n represent the number of carbons in the longest normal chain and may be the same or different and are 0 to 10, but m plus n is 10 or less, and physiologically acceptable salts thereof.

2. The compound of claim 1 wherein R² is

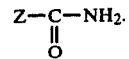

3. The compound of claim 1 wherein R² is CN.

4. The compound of claim 1 wherein R² is

5. The compound of claim 1 wherein Z is a single bond.

6. The compound of claim 1 wherein Z is

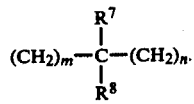

7. The compound of claim 1 wherein R³, R⁴ and R⁵ are hydrogen.

8. The compound of claim 1 having the name 5,6-dihydro-5-oxopyrazolo[1,5-c]quinazoline-2-carboxamide.

9. The compound of claim 1 having the name 5,6-dihydro-5-oxopyrazolo[1,5-c]quinazoline-2-carbonitrile.

10. A pharmaceutical composition for use in treating allergic conditions comprising an effective amount of a compound as defined in claim 1 and a pharmaceutically acceptable carrier therefor.

11. A method for treating allergic conditions in mammals, which comprises administering to the mammalian host a therapeutic amount of a compound as defined in claim 1.

* * * * *

UNITED STATES PATENT AND TRADEMARK OFFICE
CERTIFICATE OF CORRECTION

PATENT NO. : 4,337,255
DATED : June 29, 1982
INVENTOR(S) : B. Richard Vogt

It is certified that error appears in the above—identified patent and that said Letters Patent is hereby corrected as shown below:

On the Abstract page, in the title, "1,5-C" should read --1,5-c--
On the Abstract page, next to the first formula, insert --I--.
On the Abstract page, in the fourth line of formulas,

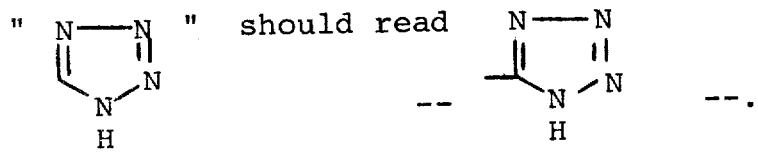

Column 1, line 37,

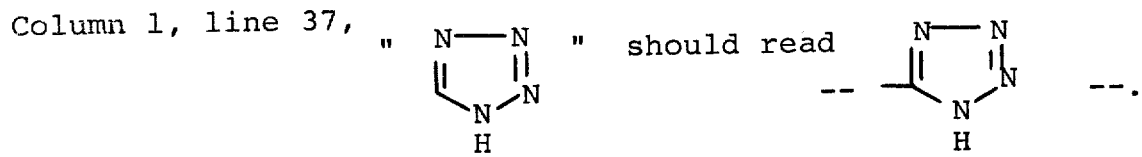

Column 2, line 3, "(CH2)m and (CH2)n" should read
--$(CH_2)_m$ and $(CH_2)_n$--.
Column 2, line 4, "stright" should read --straight--.
Column 3, lines 1-10, formula (Id) should read

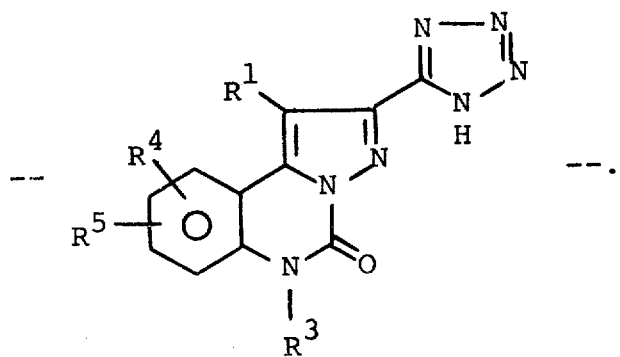

UNITED STATES PATENT AND TRADEMARK OFFICE
CERTIFICATE OF CORRECTION

PATENT NO. : 4,337,255
DATED : June 29, 1982
INVENTOR(S) : B. Richard Vogt

It is certified that error appears in the above—identified patent and that said Letters Patent is hereby corrected as shown below:

Column 4, lines 1-10, next to the formula insert --I--.
Column 7, line 67, next to the formula insert --X--.
Column 17, line 23, "amount" should read --amounts--.
Column 17, line 66, "type" should read --types--.
Column 18, line 5, "reaction" should read --reactions--.
Column 21, line 15, "18" should read -- ∿ --.
Column 22, line 55, "5(6)" should read --5(6H)--.
Column 22, line 59, after "thyl]" insert --pyrazolo-[--.
Column 24, line 49, "quinazoline" should read --quinazolin--.
Column 24, line 59, "time" should read --times--.
Column 31, Table III, Ex. 99, Col. Z, the formula should read --  --.

Column 31, Table III, Ex. 100, Col. Z the formula should read

-- 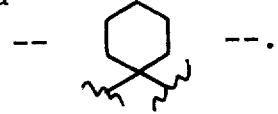 --.

Column 37, Table V, Ex. 157, Col. Z, the formula should read -- $-(CH_2)_2-$ --.
Column 38, Table VI, Ex. 183 in Col. III should read

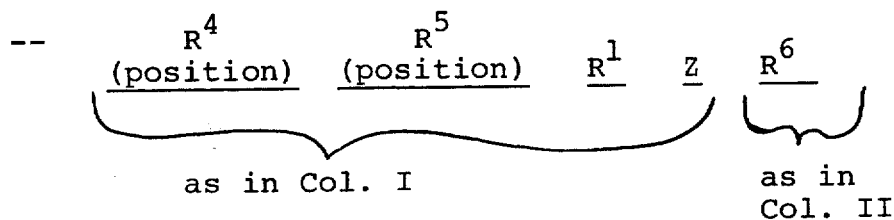

UNITED STATES PATENT AND TRADEMARK OFFICE
CERTIFICATE OF CORRECTION

PATENT NO. : 4,337,255
DATED : June 29, 1982
INVENTOR(S) : B. Richard Vogt

It is certified that error appears in the above—identified patent and that said Letters Patent is hereby corrected as shown below:

Column 41, Table VII, Ex. 219, Col. Z, the formula should read --  --.

Column 41, Table VII, Ex. 220, Col. Z, the formula should read --  --.

Column 45, Table IX, Ex. 261, Col. Z, the formula should read --  --.

Column 45, Table IX, Ex. 262, Col. Z, the formula should read -- 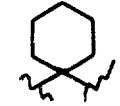 --.

Column 47, line 16, before "wherein" insert --(--.

Signed and Sealed this

Seventh Day of September 1982

[SEAL]

Attest:

GERALD J. MOSSINGHOFF

Attesting Officer  Commissioner of Patents and Trademarks